(12) United States Patent
Kenan et al.

(10) Patent No.: US 6,788,966 B2
(45) Date of Patent: Sep. 7, 2004

(54) DIAGNOSIS PROBE

(75) Inventors: Gad Kenan, Moshav Habonim (IL); Yael Agi Glickman, Haifa (IL); Orna Filo, Zurit (IL)

(73) Assignee: TransScan Medical Ltd., Migdal-Haemek (IL)

( * ) Notice: Subject to any disclaimer, the term of this patent is extended or adjusted under 35 U.S.C. 154(b) by 242 days.

(21) Appl. No.: 10/033,017

(22) Filed: Oct. 22, 2001

(65) Prior Publication Data

US 2003/0078482 A1 Apr. 24, 2003

(51) Int. Cl.$^7$ ................................................ A61B 5/04
(52) U.S. Cl. .................. 600/372; 600/373; 600/393; 600/547
(58) Field of Search ............................... 600/372, 373, 600/393, 547, 548; 607/115, 116

(56) References Cited

U.S. PATENT DOCUMENTS

| | | | |
|---|---|---|---|
| 4,291,708 A | | 9/1981 | Frei et al. |
| 4,458,694 A | | 7/1984 | Sollish et al. |
| 4,461,304 A | * | 7/1984 | Kuperstein .................. 600/378 |
| 4,969,468 A | * | 11/1990 | Byers et al. ................ 600/373 |
| 5,353,802 A | | 10/1994 | Ollmar |
| 5,524,338 A | * | 6/1996 | Martyniuk et al. ......... 600/378 |
| 5,557,213 A | | 9/1996 | Reuter et al. |
| 5,591,139 A | * | 1/1997 | Lin et al. .................... 604/264 |
| 5,641,315 A | | 6/1997 | Swart et al. |
| 5,810,742 A | | 9/1998 | Pearlman |
| 6,026,323 A | | 2/2000 | Skladnev et al. |
| 6,120,493 A | * | 9/2000 | Hofmann .................... 604/506 |

FOREIGN PATENT DOCUMENTS

| | | |
|---|---|---|
| GB | 2 138 148 | 10/1984 |
| GB | 2 276 326 | 9/1994 |
| WO | WO 01/43630 | 6/2001 |
| WO | WO 01/64102 | 9/2001 |

OTHER PUBLICATIONS

Prohaska et al, "A Mutielectrode For Intracortical Recordings Produced By Thin–Film Technology" Electroencephalography and Clinical Neurophysiology, 1977, 42:421–422.*

May et al, "A Tantulum–on–Sapphire Microelectrode Array" IEEE Trans. On Electron Devices, vol. ED–26, No. 12, Dec. 1979.*

Piperno, G. et al.; "Breast Cancer Screening by Impedance Measurements;"1990; Frontiers Med. Biol. Eng.; vol. 2; No. 2; pp. 111–117.

* cited by examiner

Primary Examiner—Lee S. Cohen
(74) Attorney, Agent, or Firm—Carella, Byne, Bain, Gilfillan et al.; Elliot M. Olstein; William Squire

(57) ABSTRACT

An electrode head including at least one bio-compatible electrode. The electrode head includes at least one printed circuit board (PCB) having a face area and a thickness and at least one bio-compatible electrode extending from the thickness of the at least one printed circuit board.

18 Claims, 11 Drawing Sheets

DIAGNOSIS PROBE

FIELD OF THE INVENTION

The present invention relates to systems for tissue characterization based on impedance measurements, and in particular to systems for skin cancer characterization.

BACKGROUND OF THE INVENTION

Skin cancer, such as melanoma, Basal cell carcinoma (BCC), Squamous cell carcinoma (SCC), is a type of cancer which afflicts many people. Early detection of skin cancer dramatically increases the probability of successful removal of the skin cancer. Conventional methods of skin cancer detection include visual inspection of suspected skin moles for characteristics of malignant tumors. These characteristics include asymmetry (i.e., one half of the mole does not match the other half), border irregularity (i.e., the edges are of the mole are ragged, notched or blurred), color (i.e., the pigmentation of the mole is not uniform) and diameter (i.e., the mole has a diameter greater than 6 millimeters) and are referred to together as the ABCD test. When a mole is identified as suspicious, a biopsy sample is taken for a more definite analysis. The percentage of positive cancer indications in melanoma biopsy tests is currently very low, i.e., less than 1%. In order to reduce the number of unnecessary biopsies, and to increase the rates of early identification of melanoma, a non-invasive method for identification of skin cancer, more objective and accurate than the ABCD test, is required.

In some cases, cameras are used to capture images of suspicious skin lesions, to allow follow up of the lesion. Images of a lesion are taken from different distances, chosen as a compromise between the accuracy achieved from being very close to the skin and the capturing a wide view of the surroundings by being very far from the skin. There exists, for example, a system which includes a pair of cameras for imaging skin lesions. A first camera is used for close-up images, and a second camera is used for various other distances farther from the skin.

Variations in electrical impedance have been suggested for use in detection of anomalies and various types of cancer, particularly breast cancer. For example, U.S. Pat. Nos. 4,291,708, 4,458,694, and 5,810,742 and the article, "Breast Cancer Screening by Impedance Measurements," by G. Piperno et al., Frontiers Med. Biol. Eng., Vol. 2 pp. 111–117, the disclosures of which are incorporated herein by reference, describe systems for determining the impedance between a point on the surface of the skin and some reference point on the body of the patient. With the use of a multi-element probe, a two-dimensional impedance map of an organ such as a breast can be generated. The impedance map, describing variations in impedance along the tissue of the organ, can be used for the detection of tumors and especially malignant tumors.

U.S. Pat. No. 4,291,708 to Frei, mentioned above, describes a probe for placement on a surface being imaged. A plurality of generally flat sensing elements are mounted on the probe in a generally planar arrangement or in a configuration fitting to the human breast.

UK patent application GB 2 276 326, filed Mar. 22, 1994, the disclosure of which is incorporated herein by reference, describes a bio-signal electrode which has a rough surface in order to improve the contact with the skin. Points of the rough surface penetrate the epidermal layer of the skin.

UK patent application GB 2 138 148, filed Apr. 13, 1984, the disclosure of which is incorporated herein by reference, describes mounting of electrodes on respective pneumatic or hydraulic cylinders which keep the electrodes at a common pressure level relative to the skin.

U.S. Pat. No. 5,353,802 to Ollmar, the disclosure of which is incorporated herein by reference, describes a device for depth selective measurement of impedance in the human body. The device is suggested for detection and characterization of surface phenomena in organic and biological material.

U.S. Pat. No. 6,026,323 to Skadlev, the disclosure of which is incorporated herein by reference, describes an instrument for detection of cervical cancer and other surface cancers. The instrument combines optical and electrical devices, which perform complex tests on the cervix of a patient and on other surfaces of a patient such as the skin. The instrument of the U.S. Pat. No. 6,026,323 patent includes three electrodes, which are used to sense the local impedance at the point of contact of the electrodes.

SUMMARY OF THE INVENTION

An aspect of some embodiments of the present invention relates to an electrode head that holds one or more biocompatible electrodes for in vivo impedance imaging. The electrode head comprises a rigid electrode head formed of one or more PCBs (printed circuit boards) on which the electrodes are mounted. In some embodiments of the invention, the rigid electrode head is formed of one or more rigid PCBs. Alternatively, the electrode head is formed of a plurality of PCBs, at least one of which is a flexible PCB, which are stiffened by their attachment. Generally, a rigid electrode head does not conform to the shape of a surface against which it is pressed. The use of a rigid electrode head ensures that the relative orientation of electrodes mounted on the electrode head is known and/or planar. Therefore, generation of an image from signals sensed by the electrodes is simpler relative to use of flexible PCBs. Also, a rigid electrode head serves as a more solid base for electrodes adapted to penetrate a tissue surface of a patient, as described hereinbelow for some embodiments of the invention.

In some embodiments of the invention, the one or more electrodes are mounted on one or more edges of the one or more PCBs. Optionally, the electrode head comprises a plurality of PCBs which are attached with their surface areas (i.e., faces) facing each other.

An aspect of some embodiments of the present invention relates to an electrode head including one or more electrodes protruding from one or more edges of the one or more PCBs. In some embodiments of the invention, the one or more electrodes comprise ends of conductive wires running along one or more of the PCBs. In some embodiments of the invention, the electrodes have an axis parallel to the surface of the PCB, such that the electrode contacts the skin of a patient axially. Optionally, the electrodes extend beyond the edge of the PCB. In some embodiments of the invention, the electrodes comprise sharp points, which penetrate the stratum corneum of the skin surface, without penetrating the epidermal layer. Optionally, the sharp points penetrate to a depth of between about 30–50 $\mu$m.

An aspect of some embodiments of the present invention relates to an electrode head that includes a plurality of PCBs permanently combined. Optionally, the PCBs are combined along their faces. In some embodiments of the invention, each of the PCBs is connected to at least one neighboring PCB such that at least part of the face area of the PCB covers most of the face area of the neighboring PCB.

An aspect of some embodiments of the present invention relates to a bio-medical probe including one or more sensing elements. The probe does not allow sensing of electrical signals, unless a physician presses the probe against the tissue surface with at least a minimal predetermined force. Optionally, not allowing the sensing of the electrical signals comprises not applying a stimulus signal required for sensing the signals. Alternatively or additionally, not allowing the sensing of the electrical signals comprises disconnecting a sensing circuit from the one or more sensing elements and/or marking acquired signals as invalid. Further alternatively or additionally, not allowing the sensing of the electrical signals comprises preventing contact between the sensing elements and an inspected tissue surface. In some embodiments of the invention, the probe includes a stopper which constrains the advancement of the sensing elements toward the tissue surface unless the minimal force is applied. The stopper is optionally mounted on a pressure exerting device, e.g., springs, pneumatic devices, hydraulic devices, relative to the electrodes, such that the electrodes do not contact the tissue surface, unless the probe is pressed against the surface with at least the minimal predetermined force. The minimal predetermined force is optionally selected such that the coupling between the electrodes and the tissue surface is substantially constant for pressure levels above the predetermined force. In exemplary embodiments of the invention, the minimal force comprises between about 0.25–1 kg/force, optionally about 0.5 kg/force. Thus, the coupling between the electrodes and the surface of the patient does not substantially depend on the force exerted by a physician pressing the probe against the surface of the patient.

In some embodiments of the invention, the stopper and the sensing elements are mounted on the probe in a manner that allows constrained movement relative to each other. In some embodiments of the invention, the mounting of the stopper and the electrodes allows constrained movement in only one direction, optionally in the axial direction. Optionally, the stopper surrounds the one or more sensing electrodes. In some embodiments of the invention, the stopper comprises a guard ring which keeps the tissue surrounding the sensing electrodes at an equipotential (e.g., grounded). Alternatively, the stopper is held at a different, optionally lower, potential than the potential at which tips 108 are held. In some embodiments of the invention, the electrodes are allowed to advance up to a predetermined distance (e.g., 0.5–3 mm) beyond the stopper.

An aspect of some embodiments of the present invention relates to a dual modality hand-held probe which includes an array of sensing elements for impedance imaging of a surface of a patient and a camera for acquiring visual images of the surface. In some embodiments of the invention, the hand-held probe is associated with a processor that registers the impedance images with the visual images. Alternatively or additionally, the processor analyzes the impedance images and/or visual images to provide an indication on the probability of a malignant tumor on the surface. The processor may be included within the probe or may be in communication with the probe.

An aspect of some embodiments of the present invention relates to a bio-medical probe which includes one or more electrodes with sharp points, adapted to penetrate the stratum corneum of the skin of a patient, without penetrating the epidermal layer of the skin. In an exemplary embodiment of the invention, the sharp points of the electrodes are allowed to penetrate to a depth of up to 30–50 µm.

An aspect of some embodiments of the present invention relates to using a probe with sharp points in an impedance imaging procedure for skin examination and/or analysis.

An aspect of some embodiments of the present invention relates to a skin examination and/or analysis procedure, e.g., a cancer screening procedure, in which a two-dimensional array of sensing elements is used to generate an impedance image of a skin region, for example, of a suspected anomaly on the skin. In accordance with this aspect of the present invention, a skin image is generated responsive to the measurements from the sensing elements, rather than a depth image as is performed in the above described art. Using an impedance map allows identifying properties of specific regions within the anomaly.

In some embodiments of the invention, the generated image comprises an image parallel to the array of sensing elements. Optionally, the sensing elements sense currents and each pixel in the impedance image corresponds to measurements from a single sensing element.

An aspect of some embodiments of the present invention relates to a bio-compatible electrode which includes an array of sensing elements in which the distance between adjacent elements is smaller than a millimeter. Optionally, the array comprises a two dimensional array of sensing elements. In some embodiments of the invention, the distance between adjacent sensing elements is smaller than 0.7, 0.6 or even 0.5 millimeters.

An aspect of some embodiments of the invention relates to a camera for acquiring skin images. The camera includes a few distinct focusing states for a single camera casing, but does not include complex zoom apparatus. Thus, the camera includes inexpensive apparatus, which allows acquiring skin images from a few different distances.

In some embodiments of the invention, the few distinct states include between two to four states. In an exemplary embodiment of the invention, the distinct states include a close state in which the camera is placed directly on the skin, and a remote state in which the images are acquired from a predetermined remote distance, e.g., 50, 80 or 100 centimeters.

There is therefore provided in accordance with an embodiment of the invention, an electrode head including at least one bio-compatible electrode, comprising at least one printed circuit board (PCB) having a face area and a thickness and at least one bio-compatible electrode extending from the thickness of the at least one printed circuit board.

Optionally, the at least one printed circuit board comprises a plurality of printed circuit boards attached along their face areas. Optionally, the plurality of printed circuit boards are attached with an adhesive which has at least 70% alcohol resistance.

Optionally, the at least one electrode comprises at least one electrode extending from each of the plurality of printed circuit boards (PCBs). In some embodiments of the invention, the at least one electrode extending from each of the plurality of PCBs comprises at least eight electrodes extending from each of the PCBs. Possibly, the at least one electrode comprises a plurality of electrodes which are held by the electrode head at fixed relative positions.

Optionally, the electrode head includes at least one leading wire running along the at least one PCB and wherein the leading wire is formed as a single piece with one of the electrodes. Optionally, the at least one electrode comprises at least one electrode tapered toward an end of the electrode, distal from the PCB.

There is further provided in accordance with an embodiment of the invention, an electrode head including at least one bio-compatible electrode, comprising a plurality of printed circuit boards (PCBs), and a plurality of electrodes extending from the printed circuit boards, the electrodes being held by the circuit boards at fixed relative positions.

Optionally, the plurality of electrodes comprise gold plated electrodes.

There is further provided in accordance with an embodiment of the invention, an electrode head including at least one bio-compatible electrode, comprising a plurality of printed circuit boards (PCB), each having a face area and a thickness, each of the PCBs being positioned with respect to at least one other PCB such that at least a portion of its face area overlaps most of the face area of the other PCB; and at least one bio-compatible electrode extending from at least one of the printed circuit boards.

Optionally, each of the PCBs is connected to at least one other PCB such that substantially all of its face area overlaps substantially all of the face area of the other PCB.

There is further provided in accordance with an embodiment of the invention, a bio-medical probe, comprising at least one electrode for placement on a tissue surface, a sensing circuit adapted to acquire signals impinging on the at least one electrode, wherein the sensing circuit is adapted to acquire the signals only if the at least one electrode is pressed against the tissue surface with at least a predetermined force.

Optionally, the at least one electrode comprises a two-dimensional array of electrodes. Optionally, the electrodes of the two-dimensional array are located on a single flat plane and/or are organized in a rectangular array. Optionally, the at least one electrode comprises one or more electrodes with pointed tips adapted to penetrate the tissue surface.

Optionally, the sensing circuit is adapted to provide a user indication when the at least one electrode is pressed against the tissue surface with at least the predetermined force. Optionally, the sensing circuit is prevented from acquiring signals when the at least one electrode is pressed against the tissue surface with at least the predetermined force.

Optionally, the sensing circuit marks signals acquired when the at least one electrode is not pressed against the tissue surface with at least the predetermined force, as invalid. Optionally, the at least one electrode does not contact the tissue surface unless the at least one electrode is pressed against the tissue surface with at least the predetermined force. Optionally, the probe includes a stopper which prevents the at least one electrode from contacting the tissue surface unless the at least one electrode is pressed against the tissue surface with at least the predetermined force.

Optionally, the probe includes a power source for applying an equipotential to the stopper. Optionally, the probe includes at least one pressure exerting device which pushes the stopper toward the tissue surface. Optionally, the at least one pressure exerting device comprises at least one spring, pneumatic device and/or hydraulic device. Optionally, the probe includes a light source adapted to illuminate a tissue surface around which the stopper is placed. Optionally, the probe includes the predetermined force comprises between about 0.25 to 1 kilogram/force.

There is further provided in accordance with an embodiment of the invention, a bio-medical probe, comprising at least one electrode for placement on a tissue surface; and a stopper coupled to the at least one electrode in a manner which allows relative movement of the stopper relative to the at least one electrode, and prevents the at least one electrode from passing the stopper by more than a predetermined distance.

Optionally, the at least one electrode is adapted to contact the tissue surface only when the stopper is pressed against the tissue surface by at least a predetermined force. Optionally, the probe includes a power source adapted to apply an equipotential to the stopper. Optionally, the stopper is coupled to the at least one electrode through at least one pressure exerting device. Optionally, the pressure exerting device comprises a spring. Optionally, the at least one electrode is surrounded by the stopper.

There is further provided in accordance with an embodiment of the invention, a method of impedance imaging, comprising pressing at least one electrode against a tissue surface, such that the at least one electrode penetrates the tissue surface without penetrating the epidermis and sensing electrical signals from the at least one electrode.

Optionally, the at least one electrode penetrates the tissue surface by at least 20 $\mu$m or 70 $\mu$m. Optionally, pressing the at least one electrode against the tissue surface comprises pressing the at least one electrode against a tissue surface on which a lesion was identified. Optionally, the at least one electrode comprises a two-dimensional array of electrodes. Optionally, the method includes displaying an impedance image responsive to the signals sensed by the array of electrodes. Optionally, the at least one electrode is pointed at its distal end.

There is further provided in accordance with an embodiment of the invention, a method of examining a tissue surface of a patient, comprising placing a probe including at least one sensing element on a tissue surface, such that the at least one sensing element penetrates the tissue surface, sensing electrical signals by the at least one sensing element; and providing an indication on the tissue surface responsive to the sensed signals.

Optionally, providing the indication on the tissue surface comprises providing an impedance map of the tissue surface and/or an indication on a probability that the tissue surface includes a cancerous tumor. Optionally, the method includes identifying a suspected tissue surface anomaly and placing the probe on the tissue surface comprises placing the probe above the suspected anomaly. Optionally, placing the probe on the tissue surface comprises placing a probe which includes a plurality of sensing elements on the tissue surface. Optionally, placing the probe on the tissue surface comprises placing a probe which includes a two-dimensional array of sensing elements on the tissue surface.

Optionally, the method includes applying a stimulus signal to the patient remote from the tissue surface on which the probe is placed and wherein sensing the electrical signals comprises sensing electrical signals generated responsive to the applied stimulus signal. Optionally, the at least one sensing element penetrates the tissue surface by less than 70 $\mu$m. Optionally, the tissue surface comprises a skin surface, a cervix and/or rectum of the patient. Optionally, the at least one sensing element taper off with a sharp point.

There is further provided in accordance with an embodiment of the invention, a method of examining a tissue surface of a patient, comprising placing a probe including at least one sensing element on a tissue surface, the at least one sensing element is tapered toward the tissue surface, sensing electrical signals by the at least one sensing element; and providing an indication on the tissue surface responsive to the sensed signals.

Optionally, the sensing elements have a triangular shape pointed toward the tissue surface. Alternatively or additionally, the sensing elements have a concave shape facing the tissue surface. Further alternatively or additionally, the sensing elements have a convex shape facing the tissue surface. Optionally, the method includes identifying a suspected tissue surface anomaly and placing the probe on the tissue surface comprises placing the probe above the suspected anomaly.

There is further provided in accordance with an embodiment of the invention, a method of examining a skin surface of a patient, comprising identifying a suspected skin lesion, placing a probe including a plurality of sensing elements on a skin surface above the identified lesion, sensing electrical signals by the plurality of sensing elements; and generating an impedance map responsive to the sensed signals.

Optionally, identifying the suspected lesion comprises visually identifying the lesion. Optionally, the plurality of sensing elements are included in a planar array of elements and wherein generating the impedance map comprises generating a map parallel to the planar array. Optionally, generating the map comprises generating a map in which each pixel corresponds to a respective sensing element of the plurality of sensing elements. Optionally, generating the impedance map comprises generating a map including at least 32, 64, 128 or 256 pixels. Optionally, the method includes acquiring at least one impedance map of an area adjacent the skin lesion but not including the skin lesion. Optionally, the method includes providing a malignancy level indication responsive to the sensed electrical signals and the at least one impedance map of an area adjacent the skin lesion.

Optionally, generating the impedance map responsive to the sensed signals is performed using at least one parameter selected responsive to the at least one impedance map of an area adjacent the skin lesion. Possibly, generating the impedance map responsive to the sensed signals comprises dividing the value of each pixel by a respective value of the at least one impedance map of an area adjacent the skin lesion. Optionally, acquiring the at least one impedance map comprises acquiring at least two impedance maps on opposite sides of the lesion. Optionally, the method includes acquiring at least one optical image of the lesion. Optionally, acquiring the at least one optical image of the lesion comprises acquiring at least one close-up image and at least one far shot image.

There is further provided in accordance with an embodiment of the invention, an electrode head including an array of bio-compatible sensing elements, comprising a substrate, and a plurality of sensing elements mounted on the substrate such that the distance between each two neighboring sensing elements is smaller than 1 mm. Optionally, the plurality of sensing elements are organized in a rectangular array. Optionally, the distance between each two neighboring sensing elements is smaller than 0.5 mm.

There is further provided in accordance with an embodiment of the invention, a probe for skin cancer examination, comprising a hand held casing, an impedance probe, adapted to sense electrical signals from a tissue surface, encased in the hand held casing, and a camera, adapted to acquire images of the tissue surface, encased in the hand held casing.

Optionally, the camera has a predetermined number of distinct focusing states.

There is further provided in accordance with an embodiment of the invention, a camera for acquiring images of skin lesions, comprising an image acquiring unit adapted to acquire images of tissue surface lesions, and a lens adapted to be positioned in a plurality of distinct focusing positions, which determine the focus distance of an image from the lens.

Optionally, the lens has only two distinct focusing positions. Optionally, one focusing position is adapted for acquiring images when the camera is placed on the tissue surface. Alternatively or additionally, one focusing position is adapted for acquiring images when the camera is distanced from the tissue surface by at least 50 cm.

Optionally, the camera does not include zoom apparatus.

There is further provided in accordance with an embodiment of the invention, a method of examining a patient, comprising identifying a suspected lesion, acquiring at least one first impedance measurement of an area surrounding the suspected lesion but not including the suspected lesion, acquiring at least one second impedance measurement including at least a portion of the lesion, and providing an indication on the lesion responsive to the at least one second impedance measurement, wherein acquiring the at least one second impedance measurement or providing the indication is performed using at least one parameter having a value determined responsive to the at least one first impedance measurement.

Optionally, identifying the lesion comprises identifying a tissue surface lesion.

In some embodiments of the invention, identifying the tissue surface lesion comprises identifying a cervix or skin lesion. Optionally, acquiring the at least one first impedance measurement comprises acquiring an impedance image comprising a plurality of pixels. Optionally, acquiring the at least one second impedance measurement comprises acquiring an impedance image of the lesion which includes a plurality of pixels.

Optionally, providing the indication comprises displaying the impedance image of the lesion. Optionally, the at least one parameter comprises a normalization parameter. Optionally, the at least one normalization parameter comprises a normalization map which includes for each pixel of the impedance image a respective normalization value.

There is further provided in accordance with an embodiment of the invention, a method of providing an indication on a malignancy level of an anomaly, comprising generating a multi-pixel impedance image of the anomaly, each pixel having a value of an image impedance related parameter, selecting a sub-group of pixels of the impedance image, including fewer pixels than included in the image, at least partially based on information external to the impedance image, and providing an indication on the malignancy level of the anomaly responsive to the value of the image impedance related parameter of the selected sub-group of pixels.

Optionally, generating the impedance image of the anomaly comprises generating an impedance image of a skin anomaly. Possibly, selecting the sub-group of pixels comprises selecting solely responsive to information external to the impedance image.

Optionally, selecting the sub-group of pixels comprises selecting responsive to an additional impedance image in which each pixel has a value of an additional impedance related parameter. Optionally, the impedance related parameter comprises a conductance measured at a specific image frequency. Optionally, the additional impedance related parameter comprises a conductance measured at a second frequency different from the specific image frequency. Possibly, selecting the sub-group of pixels comprises selecting responsive to an optical image of the anomaly. Optionally, selecting the sub-group of pixels comprises selecting a predetermined number of pixels and/or selecting pixels at positions which fulfill a predetermined requirement.

BRIEF DESCRIPTION OF THE DRAWINGS

Exemplary non-limiting embodiments of the invention will be described with reference to the following non-limiting description of exemplary embodiments, in conjunction with the figures. Identical structures, elements or parts which appear in more than one figure are preferably labeled with a same or similar number in all the figures in which they appear, in which.

DETAILED DESCRIPTION OF EMBODIMENTS

Figure 1:
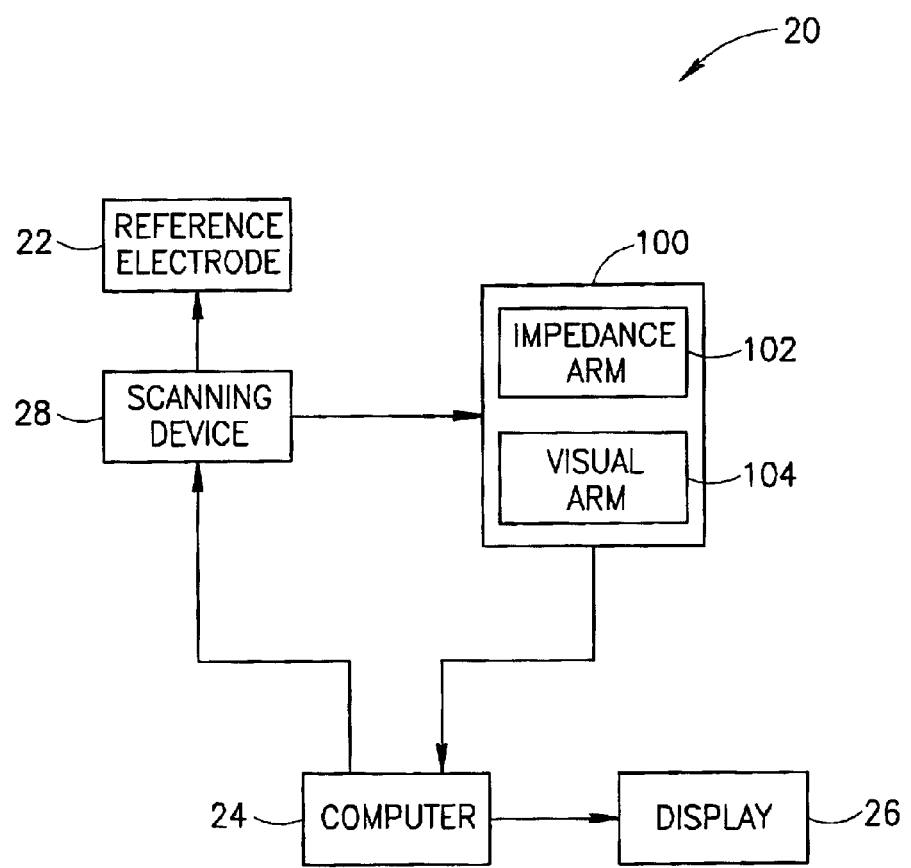
FIG. 1 is a schematic block diagram of a tissue diagnosis system, in accordance with an embodiment of the present invention.

FIG. 1 is a schematic block diagram of a tissue diagnosis system 20, in accordance with an embodiment of the present invention. Diagnosis system 20 comprises a scanning unit 100, which acquires information on an examined skin surface of a patient. In some embodiments of the invention, system 20 is used in skin screening tests for skin cancer detection. In some embodiments of the invention, scanning unit 100 comprises an impedance probe 102 which senses electrical signals from the skin surface and an optical probe 104 which collects visual images of the skin surface. The sensed electrical signals are optionally used in determining the impedance of the examined skin surface and to provide, accordingly, an indication as to whether the skin includes a malignant tumor. Optical probe 104 is optionally used to capture images of a suspected skin area at different times so that changes in appearance of the area can be determined easily.

Optionally, system 20 comprises a reference electrode 22, for example a hand held cylinder, which is used to apply a stimulus signal (e.g., a voltage or current signal) to the patient. In some embodiments of the invention, electrode 22 is held in a hand of the patient. Optionally, the stimulus signal is applied from a position remote from an examined skin surface. Alternatively or additionally, electrode 22 applies signals from a position adjacent the examined skin surface, for example from an opposite side of an organ covered by the skin.

In some embodiments of the invention, system 20 comprises a computer 24, for example, a general purpose computer with suitable software, a dedicated computer or a suitable microprocessor, which processes the acquired images and/or signals so as to provide information regarding the skin surface to a user. In some embodiments of the invention, system 20 comprises a display 26 that displays images acquired by scanning unit 100. The displayed images are optionally customized for cancer detection, in accordance with any known display method, such as any of the methods described in U.S. Pat. No. 5,810,742, the disclosure of which is incorporated herein by reference. Optionally, a method which provides sharp differentiation between cancerous and non-cancerous lesions, is used. In some embodiments of the invention, the displayed images are preprocessed in order to emphasize areas with substantially different impedance then their surroundings. Alternatively or additionally, display 26 provides indications on the probability that the skin includes a melanoma or other malignant tumor, for example according to the ABCD test. In some embodiments of the invention, computer 24 stores visual and/or impedance images of a specific skin area for later reference in order to allow easy follow-up of the progression of a skin anomaly.

In some embodiments of the invention, system 20 comprises an electrical impedance scanning device 28 which controls the sensing of the impedance signals and the applying of stimulus signals to the patient. Scanning device 28 may be substantially any suitable electrical impedance scanning device known in the art, for example, a T-Scan™ 2000 Impedance Scanner of TransScan, Israel, or as described in U.S. Pat. Nos. 5,810,742, 4,458,694, PCT application PCT/IL00/00127, filed Mar. 1, 2000, PCT application PCT/IL00/00839, filed Dec. 14, 2000 and/or U.S. patent application Ser. No. 09/460,699, filed Dec. 14, 1999, the disclosures of which documents are incorporated herein by reference. Alternatively or additionally, some or all of the tasks of scanning device 28 are performed by computer 24 and/or by scanning unit 100.

Figure 2:
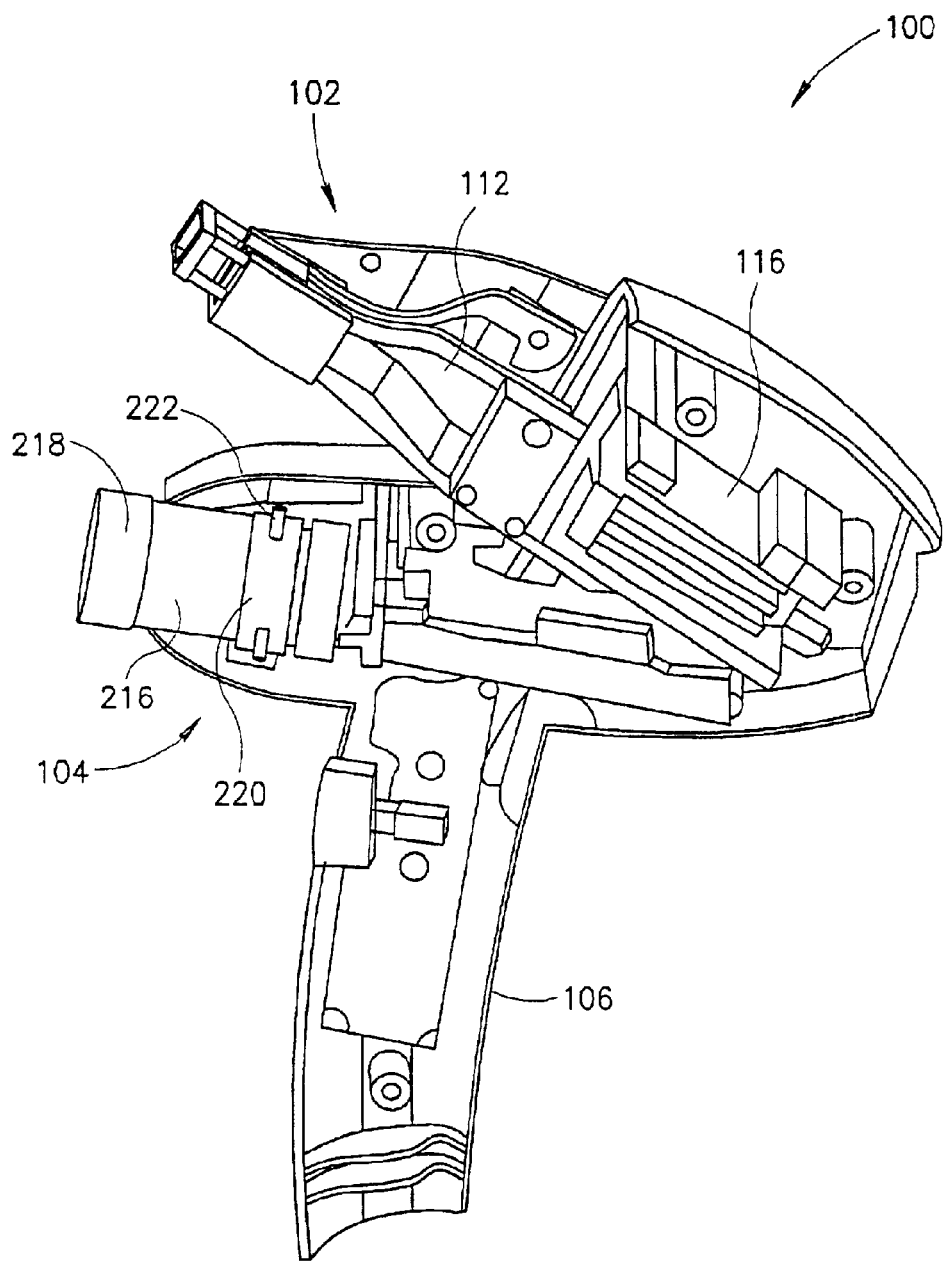
FIG. 2 is a schematic illustration of a scanning unit, in accordance with an embodiment of the present invention.

FIG. 2 is a schematic illustration of a scanning unit 100, in accordance with an embodiment of the present invention. As shown in FIG. 2, scanning unit 100 comprises an impedance probe 102, an optical probe 104 and a control handle 106. Including both probes 102 and 104 in a single scanning unit 100 allows simple diagnosis of skin tumors with both impedance and optical methods, as described hereinbelow.

Figure 3:
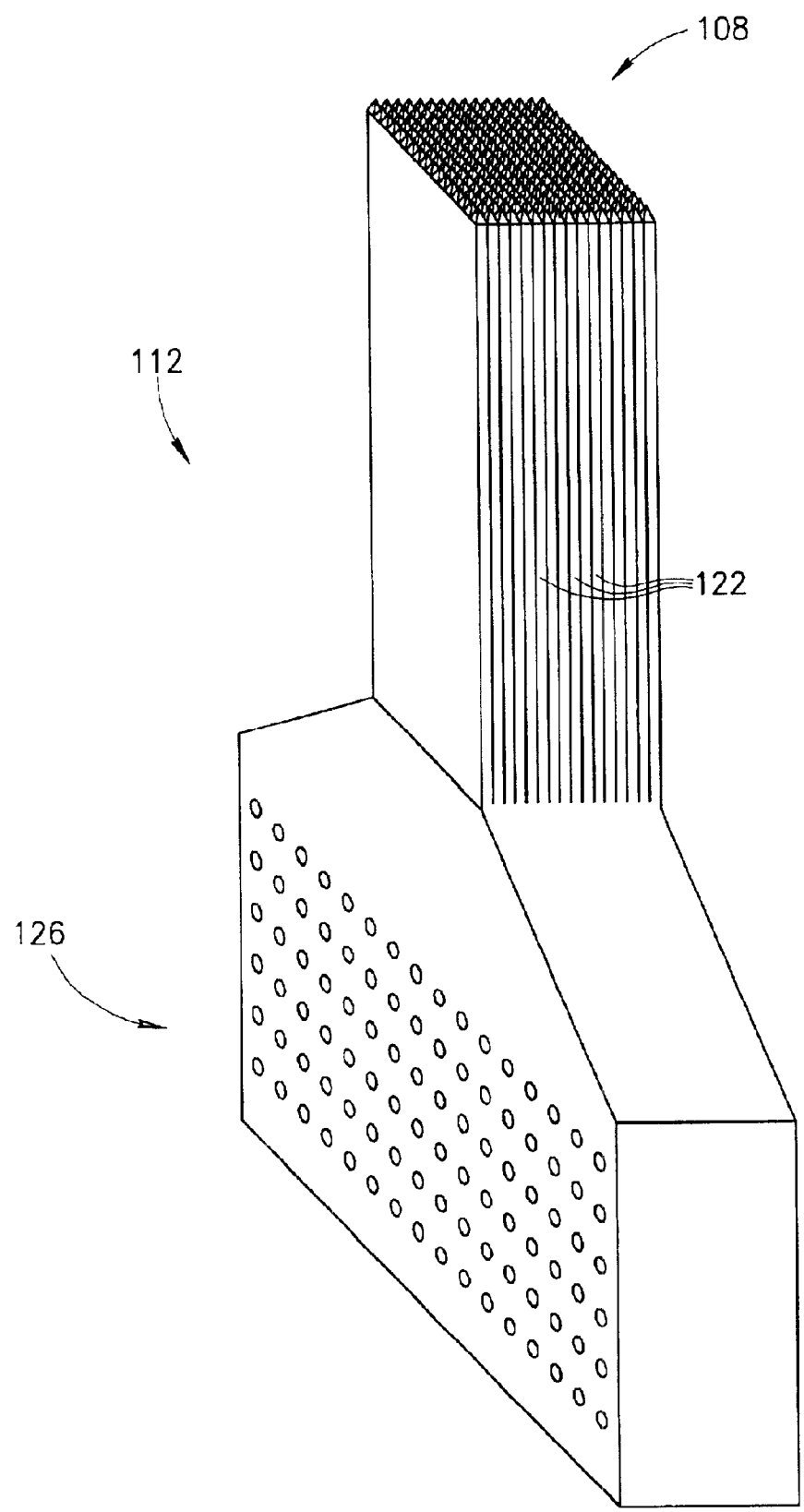
FIG. 3 is a schematic enlarged view of an electrode head for skin examination, in accordance with an embodiment of the present invention.

In some embodiments of the invention, impedance probe 102 receives an electrode head 112, which collects impedance measurements. Optionally, impedance probe 102 comprises one or more electronic boards 116, which control the operation of impedance probe 102 and/or process the electrical signals sensed by sensing tips 108 (as shown in FIG. 3). Alternatively, the control and/or processing are performed by scanning device 28 and/or computer 24, in which case electronic boards 116 may be omitted or simplified.

FIG. 3 is a schematic enlarged view of electrode head 112, in accordance with an embodiment of the present invention. Electrode head 112 comprises a plurality of sensing tips 108 which are adapted to contact the skin of a patient, and sense signals from the skin. At an opposite end to tips 108, electrode head 112 optionally includes a socket 126, which connects to a compatible plug in impedance probe 102, so as to transfer the signals sensed from tips 108 to electronic boards 116 (FIG. 2).

In some embodiments of the invention, electrode head 112 comprises a two-dimensional array of sensing tips 108, e.g., 8×16, 8×8 or 16×16, although substantially any other arrangement of sensing tips and/or number of sensing tips may be used. For example, sensing tips 108 may be arranged in concentric circles. In some embodiments of the invention, electrode head 112 comprises a plurality of printed circuit boards (PCBs) 122 which each includes a one-dimensional linear array of sensing tips 108.

In some embodiments of the invention, each of PCBs 122 includes a row (e.g., 8–16) of tips 108. In an exemplary embodiment of the invention, electrode head 112 comprises eight PCBs 122. Optionally, the distance between the centers of two adjacent PCBs 122 is between about 0.4–0.6 mm, for example 0.56 mm, which includes 0.12–0.25 mm for the thickness of PCBs 122 and 0.25–0.35 mm for isolating layers between the PCBs.

Figure 4:
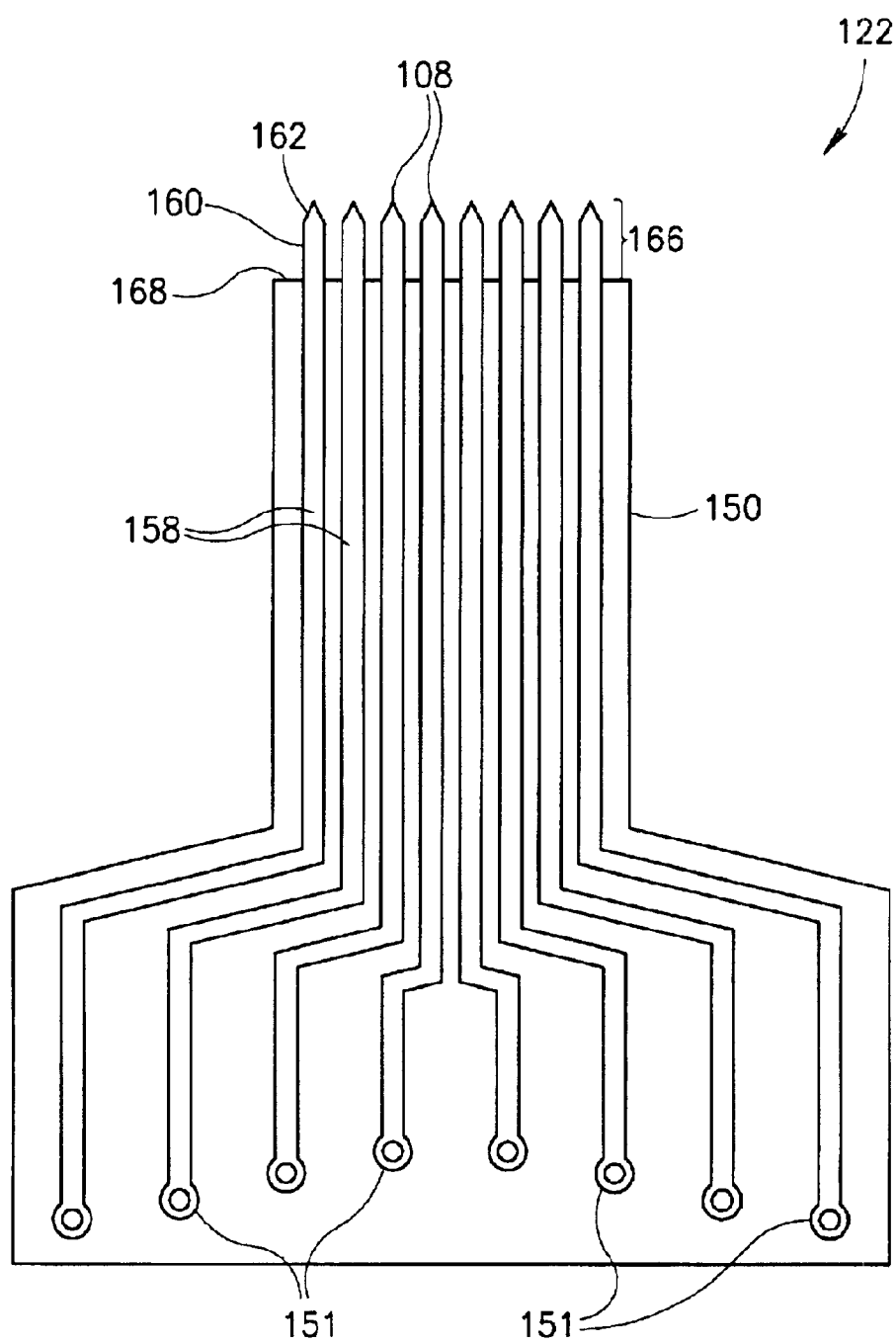
FIG. 4 is a schematic enlarged illustration of a printed circuit board used in conjunction with bio-electrodes, in accordance with an embodiment of the present invention.

Reference is also made to FIG. 4, which is a schematic enlarged illustration of a PCB 122, in accordance with an exemplary embodiment of the present invention. PCB 122 comprises an insulating substrate 150. Beyond a distal end 168 of substrate 150, PCB 122 includes a plurality of tips 108. At a proximal end of substrate 150, PCB 122 includes, for each tip 108, a respective electrical interface 151 which electrically connects the tip to socket 126 (FIG. 3). A plurality of conductive wires 158, deposited on PCB 122, run along the PCB, to connect tips 108 to electrical interfaces 151. In some embodiments of the invention, tips 108 are formed as portions 166 of conductive wires 158, protruding beyond the distal end of substrate 150. Alternatively, tips 108 are formed of different materials and/or are produced separately from conductive wires 158.

In an exemplary embodiment of the invention, conductive wires 158 have a width of between about 0.3–0.45 mm, for example 0.4 mm. Optionally, conductive wires 158 have substantially the same width over their entire length. Alternatively, conductive wires 158 are wider near electrical interfaces 151 than near tips 108. In some embodiments of the invention, PCB 122 is wider near socket 126 than near tips 108, so as to allow using wide conductive wires 158 with lower resistance, while having tips 108 relatively close to each other. Conductive wires 158 are optionally separated by between about 0.15–0.25 mm so as to prevent cross talk between wires 158. In some embodiments of the invention, conductive wires 158 comprise copper, gold, silver, and/or any other suitable conductive material.

In some embodiments of the invention, protruding portion 166 tapers off into triangular tips 108. Optionally, tips 108 are sharp at their distal end, such that during an impedance measurement session of a patient, tips 108 at least partially penetrate a tissue surface of the patient, as described hereinbelow. Optionally, substantially all of tips 108 end at the same height. In some embodiments of the invention, protruding portion 166 of a conductive wire 158 comprises a rectangular proximal portion 160 and a triangular distal portion 162. In an exemplary embodiment of the invention, triangular portion 162 has a base of between about 200–400 μm and a height of between about 150–250 μm.

Alternatively to triangular distal portion 162, protruding portion 166 has a narrow width over its entire length. Optionally, at least a portion of conductive wires 158 on substrate 150 have the same width as protruding portion 166, so as to simplify the production of tips 108 (e.g., eliminating the need to cut the tips). The remaining, proximal, portion of conductive wires 158 optionally has a larger width, so as to minimize the resistance of conductive wires 158. Further alternatively, protruding portion 166 taper off to tips 108 with a concave or convex parabolic shape. In an exemplary embodiment of the present invention, the shape of protruding portion 166 is chosen based on the specific material of the conductive wires 158 and/or the production method used to produce PCB 122. The shape of tips 108 is optionally chosen according to the depth to which the tips are to penetrate the tissue surface and/or the pressure to be exerted on the tips.

Figure 5:
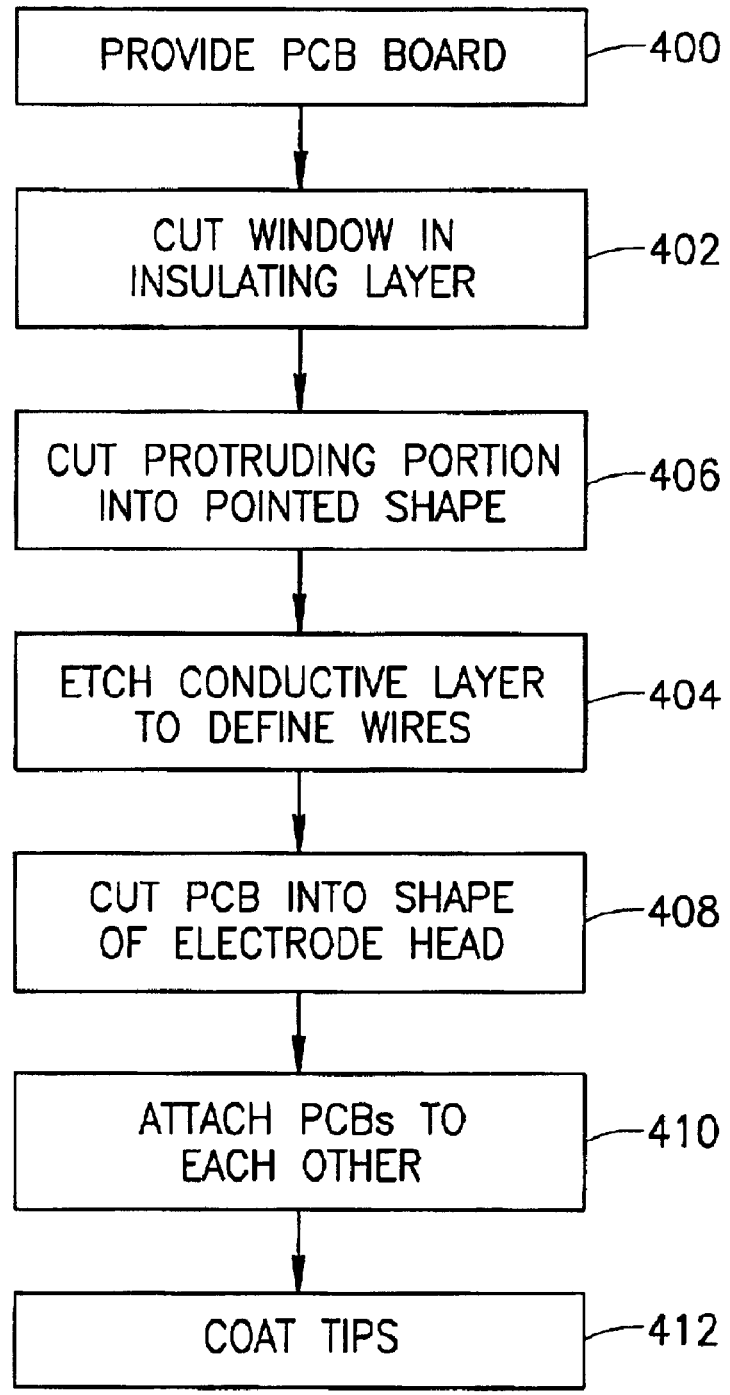
FIG. 5 is a flowchart of the acts performed in production of the electrode head of FIG. 3, in accordance with an embodiment of the present invention.
Figure 6A:
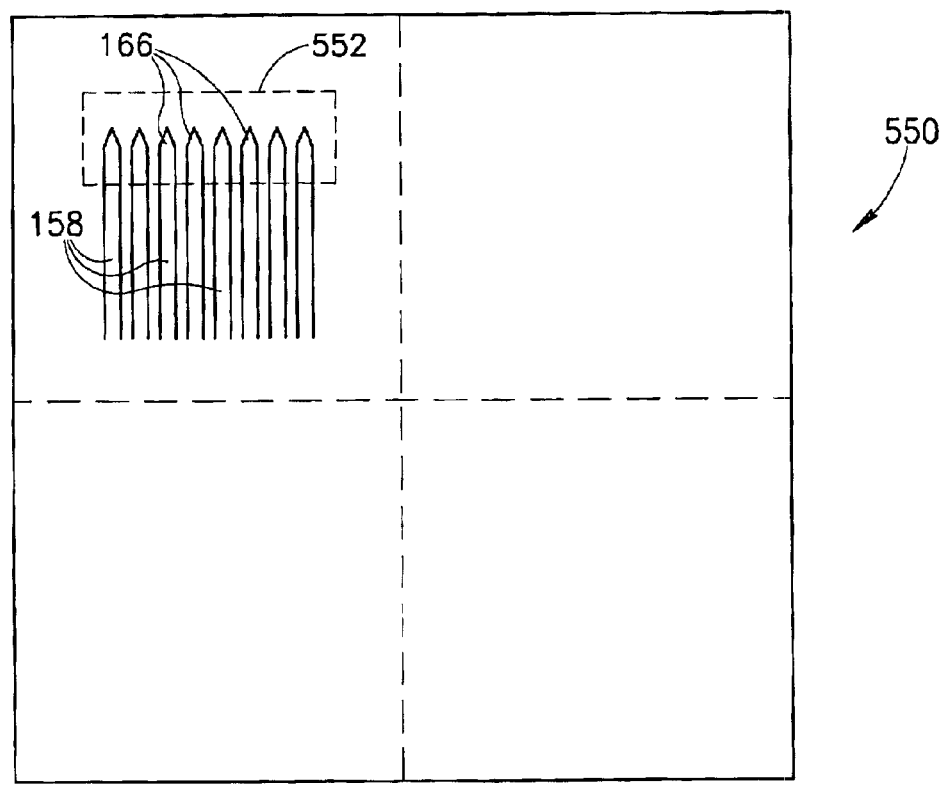
FIG. 6A is a schematic illustration of a method of producing PCB boards used in forming an electrode head, in accordance with an embodiment of the present invention.
Figure 6B:
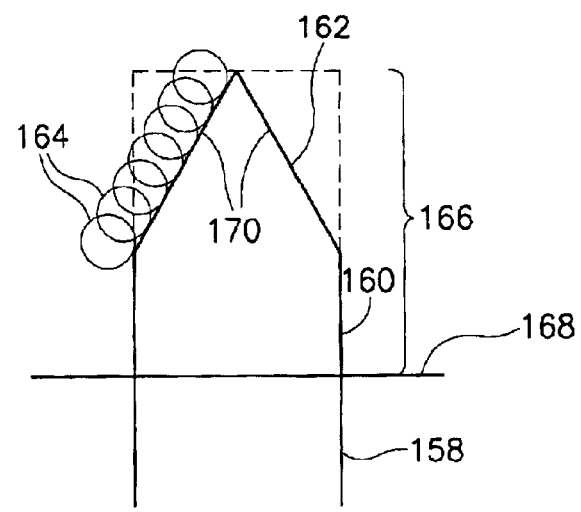
FIG. 6B is a schematic illustration of a method of producing a tip of an electrode head, in accordance with an embodiment of the present invention.

FIG. 5 is a flowchart of the acts performed in producing electrode head 112, in accordance with an embodiment of the present invention. Reference is also made to FIGS. 6A and 6B, which are schematic (out of scale) illustrations of a process of producing a plurality of PCBs 122, in accordance with an embodiment of the present invention. A single-sided copper laminated PCB board 550 including an insulating layer and a conductive layer, is provided (400). PCB board 550 is optionally used to produce a plurality of PCBs 122. In an exemplary embodiment of the invention, 72 PCBs 122 are produced from a single PCB board 550. It is noted, however, that the number of PCBs 122 produced from PCB board 550 depends on the relative sizes of PCBs 122 and PCB board 550 and the manufacture process used. The acts now described in producing a PCB 122 are optionally performed concurrently for all the PCBs produced from PCB board 550 or are repeated for each area of PCB board 550 from which a PCB 122 is produced. Alternatively or additionally, each PCB 122 is produced from a separate PCB board 550.

For each planned PCB 122, a window 552 is optionally cut (402) in the insulating layer of PCB 550, while leaving the conductive layer substantially intact. In some embodiments of the invention, protruding portions 166 are cut (406) into shape, using laser cutting or drilling methods known in the art. Optionally, a plurality of overlapping circles 164 (e.g., having about a 0.4 mm diameter) are drilled along diagonal lines 170 so as to form triangular portion 162, as shown in FIG. 6B. Alternatively, protruding portions 166 are cut using any other method.

Thereafter, conductive wires 158 are etched (404) out of the conductive layer of PCB board 550, according to a predetermined mask, using methods known in the art. The etched wires 158 optionally include protruding portions 166 which protrude into the area of window 552, where the conductive layer is not backed by an isolating layer. Optionally, wires 158 are etched (404) with a substantially uniform width in the areas of windows 552.

PCBs 122 are then optionally cut (408), in the shape of electrode head 112, out of PCB board 550. In some embodiments of the invention, a predetermined number of PCBs 122 are firmly attached (410) to each other, attaching a side with conductive wires 158 of one PCB 122 to an isolating side (not including conductive wires 158) of another PCB 122, in a manner which isolates conductive wires 158 of the different boards from each other. Optionally, PCBs 122 are attached using a suitable adhesive. Alternatively or additionally, PCBs 122 are laminated one on top of the other and/or are heat pressed against each other. In an exemplary embodiment of the present invention, PCBs 122 are attached with at least 70% alcohol resistance, so as to allow disinfecting and/or cleaning of scanning unit 100 using alcohol, without endangering the bonding of electrode head 112. Alternatively or additionally, each electrode head 112 is used for only a single patient such that alcohol disinfecting of electrode head 112 is not necessarily required and hence high resistance to alcohol may be forfeited.

In some embodiments of the invention, tips 108 resulting from the cutting (406), are coated (412) with gold and/or copper to enhance the surface contact and/or, to prevent oxygenation of the tips.

Alternatively to the production method described above, other production methods may be used. For example, instead of using a rigid PCB board, a flexible PCB board, e.g., a Kapton PCB, is used. Optionally, electrode head 112 is reinforced, so as to add rigidity to the electrode head. Using a rigid electrode head 112 provides better accuracy in the relative orientation of tips 108. Alternatively, electrode head 112 is flexible, in order to allow tips 108 to orient to the skin of a patient.

In other embodiments of the invention, protruding portions 166 are first cut out from a copper sheet not connected to an insulating layer. After protruding portions 166 are cut out and optionally also cut into their final shape, e.g., triangular, convex, concave, rectangular, the copper sheet is attached to an isolating board, in areas not including protruding portions 166. Thereafter, the etching of wires 158 is performed.

In still other embodiments of the invention, the production of PCBs 122 begins with a double-sided copper clad PCB board which is cut and etched into shape. Thereafter, isolating boards are added on both sides of the PCB board. In an exemplary embodiment of the invention, PCBs 122 comprise pre-pre glass epoxy or Pyralux AP (DuPont) double-sided copper-clad laminate with Polyimide dielectric of 50 micrometer Kapton and 1 oz copper.

Alternatively to protruding portions 166 being formed as one piece with their respective conductive wires 158, protruding portions 166 are formed separately and attached to conductive wires 158. In some embodiments of the invention, protruding portions 166 are soldered on to the edge of substrate 150. Optionally, conductive wires 158 and protruding portions 166 comprise different materials. For example, protruding portions 166 may comprise a more sturdy material than conductive wires 158. Optionally, a portion of conductive wires 158 is formed with (e.g., from the same material, at the same production stage) protruding portions 166.

Alternatively or additionally, to using a PCB board including a conductive layer and etching excess portions to form wires 158, a PCB board without a conductive layer is used and wires 158 are deposited on an isolating substrate of the PCB board, using methods known in the art. Further alternatively or additionally, PCB boards with two sided metal coating are used. The PCB boards are optionally attached with separating isolating boards between the attached boards. Further alternatively or additionally, electrode head 112 comprises a combination of flexible and rigid PCBs. For example, two rigid PCBs may be used for the extreme boards, while the interior PCBs comprise flexible PCB boards.

Figure 7:
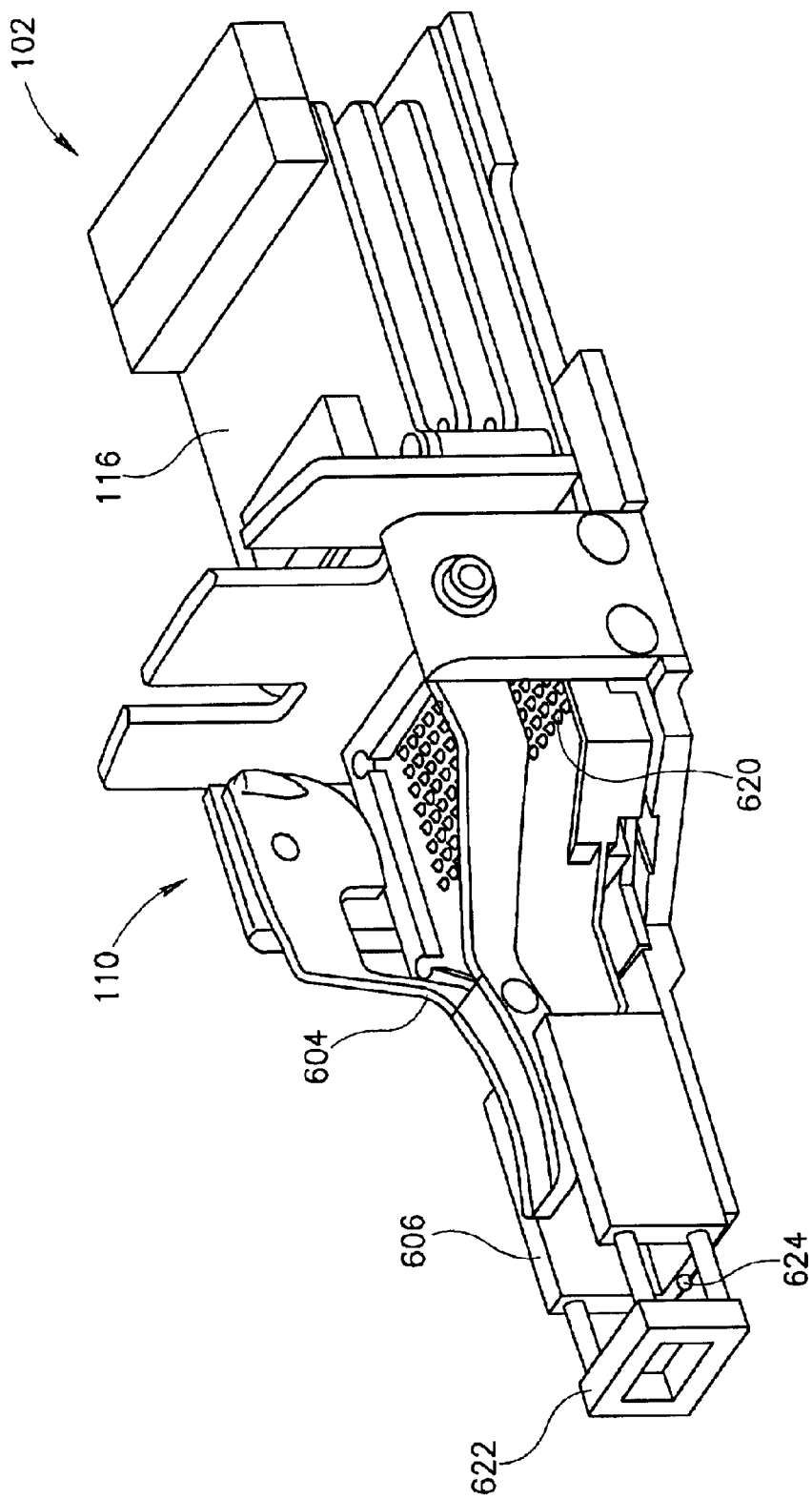
FIG. 7 is a schematic illustration of an electrode holding portion of an impedance probe, in accordance with an embodiment of the present invention.

FIG. 7 is a schematic detailed illustration of an interior portion of impedance probe 102, in accordance with an embodiment of the present invention. Impedance probe 102 optionally defines an enclave 110, sized and shaped to receive electrode head 112 (FIG. 2). Enclave 110 holds electrode head 112 in a position such that sensing tips 108 (FIG. 3) thereof protrude from a distal end of impedance probe 102.

In some embodiments of the invention, a bottom surface of enclave 110 comprises an electrical plug 620 which fits into socket 126 (FIG. 3) on electrode head 112. Optionally, electrical plug 620 comprises spring contact pins (e.g., pogo pins, available from Everett Charles Technologies (ECT), California, USA) which contact respective leads in socket 126. The use of spring contact pins allows inserting electrode heads 112 into probe 102 for a very large number of times, without plug 620 and socket 126 breaking. Thus, probe 102 can be used on a very large number of patients even if electrode head 112 is disposable and is replaced between patients. Alternatively, plug 620 comprises pins and socket 126 comprises respective holes. Optionally, the pins and holes are produced with high durability to allow insertion of electrode head 112 for a large number of times. Alternatively or additionally, the electrical connection to electrode head 112 is provided through any other coupling method and/or from any other direction, for example through a proximal end of the electrode head.

A rotateable arm 604 optionally holds electrode head 112 in place within enclave 110. As shown, arm 604 is in a closed position in which electrode head 112 is secured in place. In order to replace electrode head 112, arm 604 is lifted, allowing electrode head 112 to be removed. Alternatively or additionally, any other method is used to hold electrode head 112 in place, for example, rubber fastening, Velcro fastening and/or magnetic coupling.

In some embodiments of the invention, impedance probe 102 comprises a guard ring 622 at a distal end thereof. Optionally, guard ring 622 is mounted on a railing 606 defining a distal portion of enclave 110 through springs, which require application of a predetermined force in order to allow contact between tips 108 and a skin region of a patient. That is, in the absence of an applied force, guard ring 622 extends beyond tips 108, preventing contact between tips 108 and the skin of the patient. When probe 102 is pressed against the patient with at least the predetermined force, guard ring 622 recedes sufficiently so as to allow contact between tips 108 and the skin.

In some embodiments of the invention, guard ring 622 is coupled to railing 606 via springs (not shown), for example which are located within railing 606. Alternatively or additionally, any other pressure-applying device couples guard ring 622 to railing 606, for example hydraulic and/or pneumatic elements. Alternatively or additionally to coupling guard ring 622 to railing 606, guard ring 622 is coupled to any other part of electrode holding portion 110.

In some embodiments of the invention, guard ring 622 has a maximal receding point to which the guard ring recedes for any applied force greater than or equal to the predetermined force. The maximal receding extent of guard ring 622 optionally defines an extent to which tips 108 penetrate the tissue of the patient.

In some embodiments of the invention, the defined extent to which tips 108 penetrate the tissue surface is between about 30–100 $\mu$m, optionally about 50 $\mu$m. This penetration depth is generally sufficient to pass the outer dead cell layer of the skin, i.e., the stratum corneum, without passing too deep into the skin. The dead cell layer has a very high resistance and generally does not include anomalies that need to be inspected. Therefore, penetrating the dead cell layer does not reduce the pertinence of the sensed signals to the measurement of skin anomalies, while it reduces the masking effect of the skin tissue and increases the contrast of the sensed signals (by reducing the attenuation caused by the dead cell layer.

In some embodiments of the invention, tips 108 penetrate the dead cell layer of the skin substantially without causing pain to the patient. Alternatively or additionally, tips 108 penetrate the dead cell layer of the skin substantially without the patient noticing the penetration.

In some embodiments of the invention, impedance probe 102 comprises a user indication unit which notifies the user when sufficient force is exerted in pressing guard ring 622 against the skin of the patient. For example, a light may be lit when sufficient force is applied. Alternatively or additionally, measurements from tips 108 are taken only when sufficient force is applied.

Alternatively or additionally to pressure coupling of guard ring 622, electrode head 112 fits into enclave 110 with a predetermined positioning of tips 108 relative to guard ring 622. Optionally, the predetermined positioning defines the extent of penetration of tips 108 into the tissue surface.

Further alternatively or additionally, electrode head 112 is mounted on electrode holding portion 110 through a pressure exerting device, such as, one or more springs, hydraulic or pneumatic devices, which presses tips 108 of the electrode head towards the tissue surface of the patient. Optionally, the physician using impedance probe 102 is instructed to press electrode head 112 against the tissue surface by at least a predetermined force. In some embodiments of the invention, the pressure exerting device has a maximal pressure state and the physician is instructed to achieve this maximal pressure state. Alternatively or additionally, measurements are not possible unless the maximal pressure state or at least the predetermined force are achieved. Optionally, in this alternative, guard ring 622 is fixed to electrode holding portion 110.

In some embodiments of the invention, instead of electrode head 112, a plurality of spring contact pins (e.g., pogo pins) are used to acquire the electrical signals.

In an embodiment of the invention, all the sensing elements are held against the surface with a substantially equal pressure allowing more accurate measurements than when the pressure of the sensing elements against the surface is not controlled. Alternatively or additionally, different sensing elements are held against the surface at different controlled pressures. For example, the different pressures may be in accordance with a pattern of the currents applied to the imaged area.

Further alternatively or additionally, impedance probe 102 includes a pressure sensor which measures the pressure exerted by electrode head 112 against the skin surface of the patient and/or the pressure exerted by the skin on to guard ring 622. A physician optionally adjusts the pressure of scanning unit 100 against the surface based on the indications. Alternatively or additionally, the recording of the signals is performed automatically when a predetermined pressure is reached. Further alternatively or additionally, the acquired signals are associated with the measured pressure at the time at which they were acquired and the processing of the signals is performed as a function of the pressure.

Optionally, guard ring 622 is kept, during acquisition of electrical signals through tips 108, at a ground potential, so that side currents do not affect the signals sensed by tips 108. Thus, the influence of the skin not beneath electrode head 112 on the sensed signals is minimal. Alternatively or additionally, a separate guard ring, between guard ring 622 and tips 108 or beyond guard ring 622, is held at a ground potential. Optionally, some of tips 108, for example, the external tips, are held at a ground potential, while other tips 108 sense signals from the patient's skin. Further alternatively, a ground potential is not applied to guard ring 622 or to any other guard ring and the processing of the signals acquired by tips 108 compensates for side currents and/or uses the side currents in better determining impedance characteristics, as described, for example, in Israel patent application 142,451 filed Apr. 4, 2001, the disclosure of which is incorporated herein by reference.

Alternatively or additionally to using guard ring 622, the sharpness and/or shape of tips 108 determines the extent to which the tips penetrate the tissue surface.

In some embodiments of the invention, impedance probe 102 comprises a light source 624, which when the impedance probe is placed on a tissue surface, illuminates the tissue portion which will be measured by tips 108. The light source aids in positioning tips 108 on an anomaly which is to be imaged. In some embodiments of the invention, the light source comprises a white LED (light emission diode) that is mounted on railing 606. It is noted that during the placement of impedance probe 102 on the suspected skin anomaly, tips 108 are not pressed into guard ring 622, such that the light from light source 624 illuminates the skin against which guard ring 622 is pressed.

Referring back to FIG. 2, optical probe 104 optionally comprises a lens case 216 having two lens states. In a first state, optical probe 104 is focused for acquiring images when a distal end 218 of lens case 216 is pressed against a skin surface of the patient. In a second state, optical probe 104 is focused for acquiring images with distal end 218 at a predetermined distance from the skin surface of the patient. The predetermined distance is optionally about 50–60 centimeters, 90–100 centimeters, or any other distance which is convenient for image acquisition by a physician and/or provides data on the surroundings of a suspected skin tumor required for keeping track of the progress of the tumor.

In some embodiments of the invention, rotation of distal end 218 of lens case 216 adjusts the lens state of optical probe 104. Optionally, a stopper ring 220 including two bulging arms 222, surrounds lens case 216. Bulging arms 222 limit the rotation of distal end 218, such that a maximal rotation to the right brings optical probe 104 into the first state and a maximal rotation to the left brings optical probe 104 into the second state, or vice versa. Alternatively or additionally, any other method is used, such as button controlled electric rotation, is used to move optical probe 104 between the two states. By using an optical probe in a single casing, which allows acquiring of images in two different states, simple acquisition of both far and near images is achieved. By having only two states, rather than using a camera which focuses for a plurality of states, e.g., with a sophisticated zoom, the cost of optical probe 104 is substantially reduced.

In some embodiments of the invention, instead of two distinct optical states, optical probe 104 may have only a single state (close or far) or may have three or four distinct states. Alternatively or additionally, scanning unit 100 may include instead of optical probe 104 any optical camera known in the art. Further alternatively or additionally, impedance probe 102 and optical probe 104 may be included in separate units and/or may be supplied and/or utilized separately.

In some embodiments of the invention, optical probe 104 is periodically calibrated in order to prevent color drift over time. Optionally, the calibration includes acquiring an image of a predetermined calibration scene, e.g., a white or spectrum scene, and determining an adjustment factor, which is a function of, optionally equal to, the difference between the acquired calibration image and the predetermined known image. Images acquired by optical probe 104 are optionally adjusted by the determined adjustment factor. In some embodiments of the invention, the calibration is performed every week, month, year and/or according to the color drift of probe 104.

Figure 8:
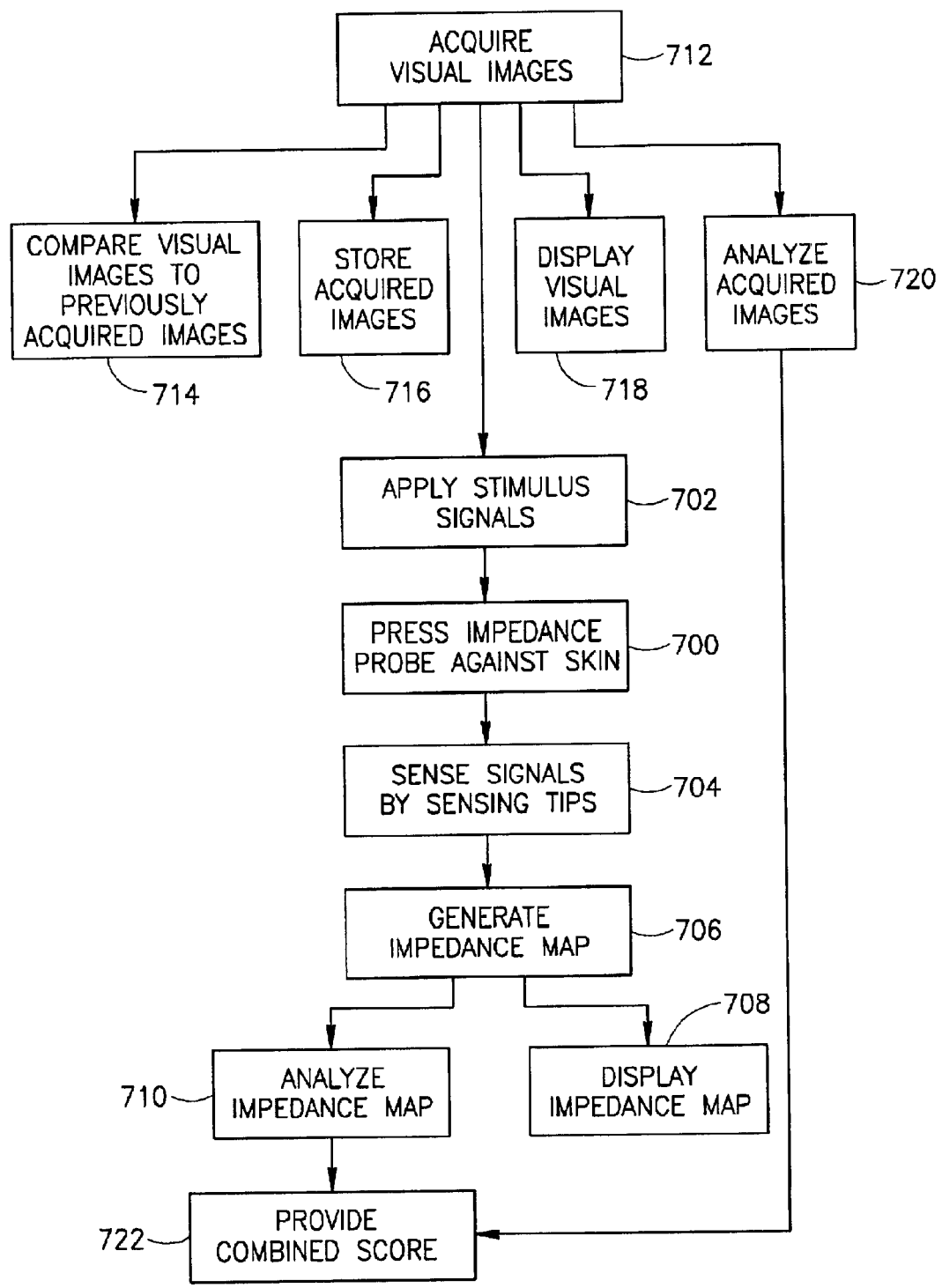
FIG. 8 is a flowchart of the acts performed during a skin examination procedure, in accordance with an embodiment of the present invention.

FIG. 8 is a flowchart of acts performed during a skin examination procedure, in accordance with an embodiment of the present invention. In examining a suspicious anomaly on the skin of a patient, one or more visual images of the examined surface are optionally acquired (712). In some embodiments of the invention, the acquired visual images are compared (714) to previously acquired visual images of the same skin surface, for example, in order to follow the progress of a suspected tumor. Alternatively or additionally, the acquired visual images are stored (716) for comparison to later acquired images. In some embodiments of the invention, the acquired images are displayed (718) on display 26. It is noted that the impedance and visual images displayed on display 26 may be transferred to any remote location for display and analysis by specialist physicians. In some embodiments of the invention, computer 24 analyzes (720) the acquired visual images to provide an indication on whether the skin surface has a suspected melanoma or other malignant tumor, for example using the ABCD test.

Thereafter, stimulus signals are optionally applied (702), at one or more frequencies, to electrode 22. Impedance probe 102 is pressed (700) against the skin surface and sensing tips 108 sense (704) signals responsive to the stimulus signals. Alternatively, the stimulus signal is applied only after impedance probe 102 is pressed against the skin surface. The sensed signals are processed to generate (706) one or more impedance maps of the skin surface. Optionally, the one or more impedance maps are displayed (708) on display 26. Alternatively or additionally, computer 24 analyzes (710) the one or more impedance maps to provide an indication on the chances of the examined skin surface including a melanoma or other malignant tumor. The impedance map shows the precise area of the skin at which specific impedance values were acquired. In addition, the use of an impedance map allows easy comparison of impedance values in different areas of the patient's skin.

In some embodiments of the invention, an impedance mapping procedure includes placing sensing tips 108 against a skin area including the suspected anomaly and acquiring one or more impedance maps. The one or more maps optionally include a plurality of maps for different stimulus signals, e.g., for different signal frequencies. Alternatively or additionally, the one or more maps include a plurality of maps taken for different placements of sensing tips 108 on the skin, in case one or more of the placements of the tips did not form good contact with the skin and/or in order to cover a large anomaly.

In some embodiments of the invention, in addition to generating maps of a skin area including the anomaly, the impedance mapping procedure includes generating control impedance maps of healthy skin adjacent the anomaly. The control impedance maps are generated before and/or after the one or more impedance maps of the anomaly. In some embodiments of the invention, the values of the pixels of the control maps are used for normalization of the anomaly maps, as described hereinbelow.

Computer 24 optionally provides (722) a combined malignancy level score based on the analysis of the visual and impedance images. Alternatively or additionally, separate malignancy scores are provided for the impedance and visual images. In some embodiments of the invention, the combined malignancy level score is a function of the area of the anomaly, the fuzziness of the anomaly and/or of one or more ABCD test values. In addition, the combined malignancy level score is optionally a function of the capacitance, conductance, phase and/or any other dielectric parameter of a selected group of pixels of the impedance image. The combined malignancy level score is optionally a weighted sum of an impedance score and an optical score.

In some embodiments of the invention, the selected group of pixels comprises a predetermined number of pixels, for example, between about 5–20 pixels, for example between 8–14 pixels. In an exemplary embodiment of the invention, the selected group of pixels comprises all the inner pixels of the impedance image, i.e., the pixels not included in the outer rows or columns. Optionally, the selected group of pixels includes pixels with a highest value of one or more dielectric parameters, at one or more frequencies. Alternatively or additionally, the selected group of pixels comprises pixels with at least a threshold value of one or more dielectric parameters. In this alternative, the number of selected pixels may be up to the maximal number of imaged pixels or may have an upper limit, e.g., between 50–80. In an exemplary embodiment of the invention, the upper limit of the number of selected pixels comprises all the inner pixels, and outer pixels are optionally never selected.

The dielectric parameters used in selecting pixels and/or in calculating the combined malignancy level score may include, for example conductance, capacitance, real and/or imaginary admittance and/or combined functions thereof. The dielectric parameters may use the real and/or imaginary portions at one or more frequencies. Further impedance related parameters determined for each frequency, which may be used, include a specific frequency which is characteristic of the pixel, other polychromatic parameters, such as described in the above mentioned U.S. Pat. No. 5,810,742, and/or characteristic frequency-dependent profiles of one or more impedance parameters. The dielectric parameters may be raw data values or may undergo any pre-processing, such as normalization using any of the normalization methods now described.

In some embodiments of the invention, a normalized impedance map is generated by dividing the value of each pixel in an anomaly map by the average values of the respective pixels (e.g., pixels in the same relative positions) in the control maps. Alternatively or additionally, the same normalization value is used for all the pixels of the anomaly map, for example, the average value of all the pixels of the control maps. Further alternatively or additionally, values of pixels in the anomaly map, which relate to areas beyond the anomaly are used to normalize the values of the anomaly map. Optionally, the normalization value is an average value of pixels not belonging to the anomaly. The pixels not belonging to the anomaly may be identified using any method known in the art, such as pixels having low conductance values and/or pixels remote from the selected anomaly pixels.

In some embodiments of the invention, a plurality of complex admittance maps at different frequencies are generated. In an exemplary embodiment of the invention, the admittance maps are generated for 19 frequencies in the range frequency 100 Hz–500 kHz. It is noted, however, that any other number of maps may be generated and/or other frequency ranges. For example, admittance maps may be generated for two frequencies, e.g., a contrast image and a differentiation image. Optionally, the admittance maps are normalized using any of the methods described above, for example relative to the admittance of the control images. Normalized conductance maps are then optionally derived from the normalized admittance. Optionally, 10 pixels with a highest normalized conductance at a first frequency, optionally a frequency which has a best inter-image contrast (e.g., 2 kHz), are selected. The impedance score is optionally calculated as a function of the average conductance at one or more second frequencies of the selected 10 pixels. The one or more second frequencies are optionally frequencies which best differentiate between healthy and malignant tissue (e.g., 1 kHz).

In some embodiments of the invention, the optical score is a function of the area of the anomaly and the length of the two axes of the anomaly.

Referring in more detail to applying (702) and sensing (704) the electrical signals, in some embodiments of the invention, the applied stimulus signals include a plurality of signals at different frequencies, and the sensed signals are analyzed for the different frequencies. Alternatively or additionally, the applied stimulus signals include signals with specific amplitudes, phases and/or from specific positions, for example, as described in any of the above patent applications mentioned above with reference to scanning device 28.

In some embodiments of the invention, before placing (700) impedance probe 102 on the tissue surface, the tissue surface is cleaned with alcohol and/or is dampened with a saline solution.

In some embodiments of the invention, scanning unit 100 is used for examining a plurality of patients. Optionally, between patients, guard ring 622 is cleaned and/or disinfected, for example with alcohol, and electrode head 112 is replaced with a new electrode head. In some embodiments of the invention, electrode head 112 is produced using cheap, mass production methods so as to allow large scale melanoma or other skin cancer screening procedures at low cost. Optionally, between patients, a physician also enters the ID of the next patient to allow retrieval and/or storage of optic and/or impedance information in a user file and/or performs a calibration process for the next patient.

In some embodiments of the invention, as described with reference to FIG. 8, an examination procedure begins with acquiring optical images and later includes acquiring impedance images. Thus, the optical images are acquired before tips 108, which may obscure the images, are pressed against the skin and before the skin is wetted with a saline solution. Alternatively or additionally, in at least some examination procedures, the optical images are acquired before the impedance measurements are performed. Thus, the number and/or type of optical images to be acquired may be determined responsive to the impedance measurements. For example, fewer images may be acquired when the impedance readings indicate no malignancy, relative to the number of images acquired when the impedance readings indicate malignancy. Optionally, in this alternative, before acquiring the optical images, the skin surface is dried to remove saline liquids used in the impedance mapping.

In some embodiments of the invention, computer 24 registers the impedance and visual images relative to each other. Optionally, in those embodiments in which optical images are acquired after the impedance images, when impedance probe 102 is placed (700) against the skin, it leaves a registration mark on the skin, which later appears in the acquired optical images. For example, impedance probe 102 may imprint one or more ink marks, optionally on peripheral areas of the examined area (for example on the guard ring described hereinbelow). Alternatively or additionally, a physician performing the examination passes a pen or marker around impedance probe 102 on the examined skin, before and/or after sensing (704) the electrical signals. Optionally, the acquired visual images include the registration mark, and accordingly the images are registered relative to each other.

Figure 9A:
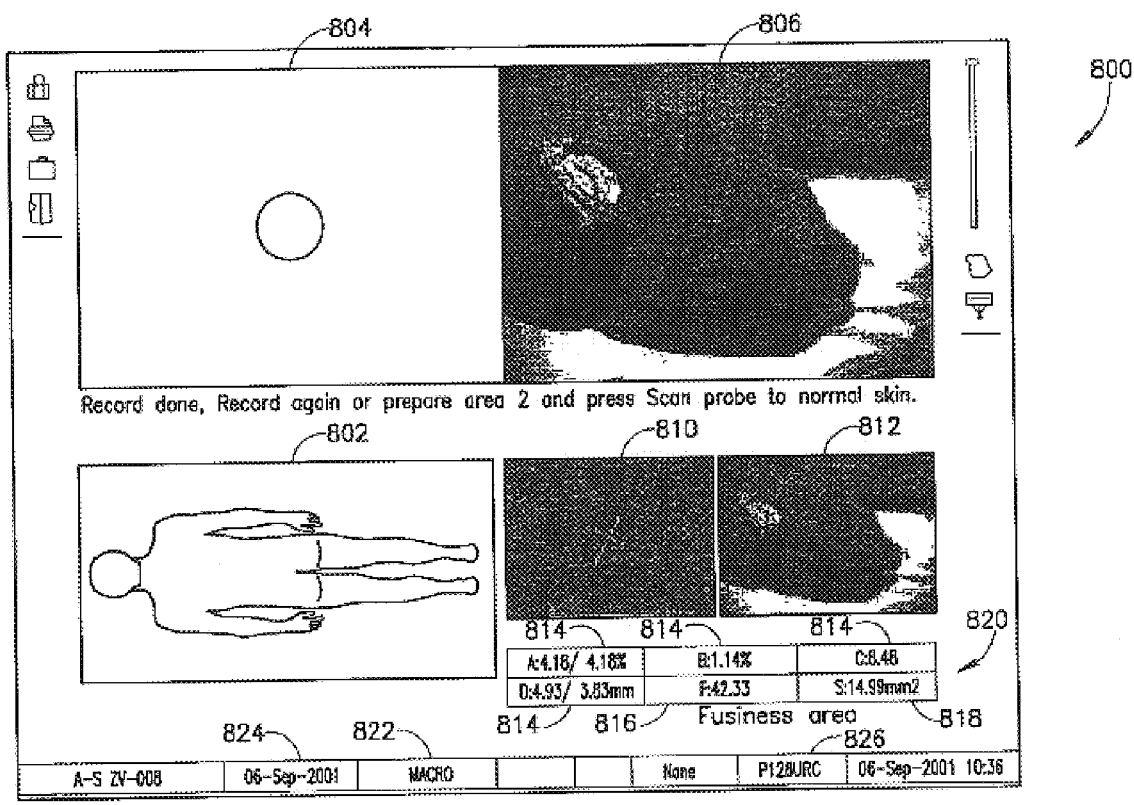
FIGS. 9A, 9B and 9C are schematic illustrations of display screens of a tissue diagnosis system, in accordance with an embodiment of the present invention.

FIG. 9A is a schematic illustration of an image capturing screen 800 shown on display 26, in accordance with an embodiment of the present invention. In some embodiments of the invention, after entering a patient ID, the physician acquires images of a lesion on the patient. Optionally, the physician marks the location of the lesion on a map 802 of the patient and acquires, using optical probe 104, real time video images of the lesion. Alternatively, the physician marks the location of the lesion on map 802 after acquiring one or both of the images. The real time video images are optionally continuously displayed in a real time window 804. In some embodiments of the invention, the real time images may be close up images acquired in a "micro" state or far shot images acquired in a "macro" state. Optionally, the operation state is shown in a state field 822 of screen 800.

In some embodiments of the invention, when the physician is satisfied with the image in real time window 804, the physician captures the image, for example by actuating a user control, e.g., a button, on scanning unit 100 and/or on computer 24. The captured image is optionally shown in a captured image window 806. Optionally, the physician may capture additional images, in addition to or instead of previously acquired images. In some embodiments of the invention, a close up window 810 and a far shot window 812 show representative captured images of the "micro" and "macro" states, respectively.

Optionally, the physician marks the boundaries of the lesion in close up window 810. Alternatively or additionally, computer 24 automatically draws the boundaries of the lesion according to the difference in shade between the lesion and its surroundings. In some embodiments of the invention, a data box 820 displays values of parameters of the lesion as derived from the acquired images, such as values of the ABCD test in fields 814, a fuzziness value in a field 816 and/or an area of the lesion in a field 818. Optionally, screen 800 shows other information, such as a check-up date 824 and/or a patient ID 826.

Figure 9B:
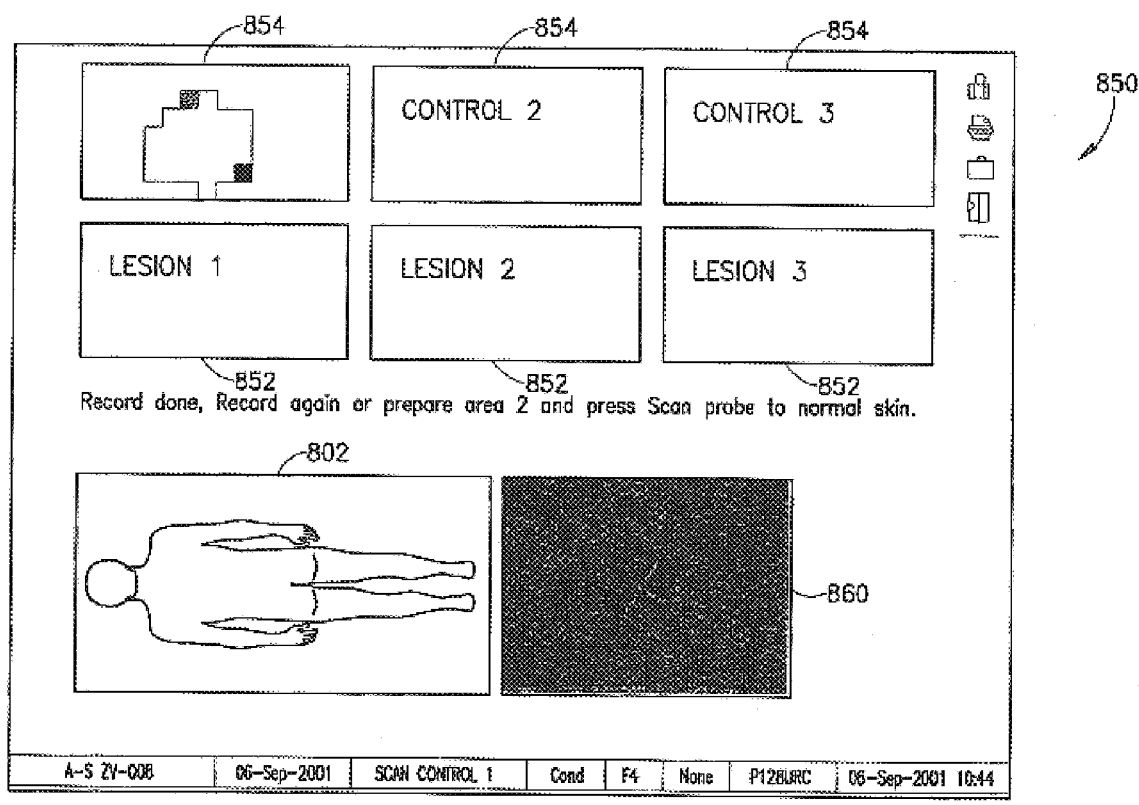

FIG. 9B is a schematic illustration of an impedance screen 850 shown on display 26, in accordance with an embodiment of the invention. Optionally, after acquiring images using optical probe 104, the physician acquires impedance maps of the lesions. Tips 108 are pressed against the lesion and one or more impedance images of the lesion are acquired and displayed in lesion windows 852. Optionally, the physician also places tips 108 on one or more healthy areas adjacent the lesion and acquires one or more control impedance images, which are displayed in control windows 854. The control impedance images may be acquired before, after or interleaved with the impedance images of the lesion. In some embodiments of the invention, impedance screen 850 also shows map 802 with the location of the lesion and/or shows an optical image of the lesion in a window 860. In some embodiments of the invention, the display and/or analysis of one or more the images in lesion windows 852 is normalized responsive to the maps in one or more of control windows 854. The normalization is optionally performed using any of the above described methods. Alternatively, the display in windows 852 and/or 854 include non-normalized control data.

In some embodiments of the invention, impedance screen 850 includes up to three lesion windows 852 and three control windows 854. Alternatively, impedance screen 850 includes any other number of windows for displaying lesion impedance images and/or control impedance images. Alternatively or additionally, each of windows 852 and/or 854 may be used for either control or lesion impedance images according to the physician's decision. Optionally, more images than displayed may be acquired and the physician selects which impedance images are to be displayed.

In some embodiments of the invention, the different lesion impedance images shown in lesion windows 852 correspond to different placements of tips 108 of impedance probe 102. For example, when a lesion is relatively large, different lesion windows 852 may show different portions of the lesion. Similarly, in some embodiments of the invention, different control windows 854 show different control areas surrounding the lesion. In an exemplary embodiment of the invention, an impedance imaging procedure includes acquiring three control impedance images surrounding the lesion, and then acquiring one or more impedance images of the lesion, depending on the size of the lesion.

Alternatively or additionally, a plurality of lesion windows 852 and/or control windows 854 show impedance images, which differ in one or more parameters, of a same region. Optionally, the impedance images in different windows 852 and/or 854 differ in the pressure applied to tips 108 when the images are acquired, the depth of penetration of tips 108 into the tissue surface, and/or the frequency of the stimulus signals. Alternatively or additionally, the impedance images differ in the displayed parameter, which may be for example real and/or imaginary parts of an admittance, conductance, capacitance and/or a complex function or derivative thereof. In some embodiments of the invention, each lesion impedance image has a respective control impedance image. Alternatively, there is no specific relation between the lesion impedance images and the control impedance images.

Figure 9C:
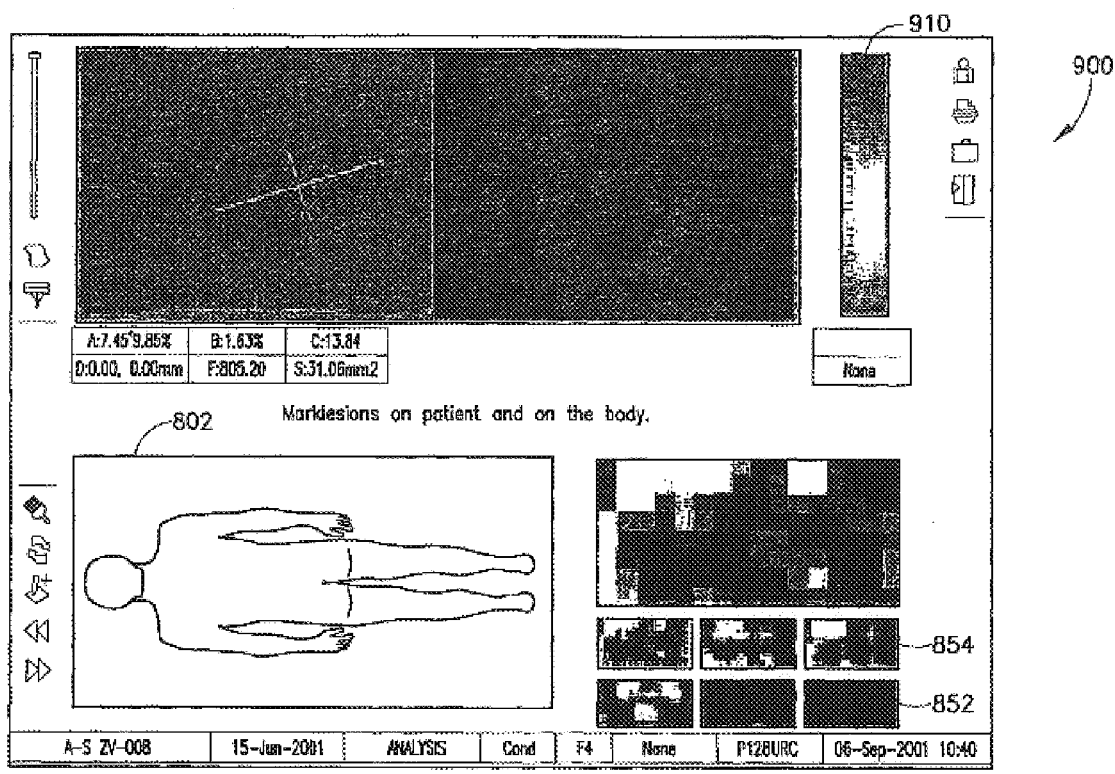

FIG. 9C is a schematic illustration of an analysis screen 900 shown on display 26, in accordance with an embodiment of the present invention. Analysis screen 900 optionally displays the information from both impedance and optical acquisition, allowing the physician to view at a single time maximal information required to analyze the lesion. In some embodiments of the invention, screen 900 includes a malignancy level bar 910 which visually displays the value of the combined malignancy level score of the lesion. Alternatively or additionally, the score is displayed as a number and/or using any other display method.

In some embodiments of the invention, the calculation of the combined malignancy level score is performed after the measurements are completed. In other embodiments of the invention, an indication on the level of malignancy of a tissue region is provided in real-time. For example, in some embodiments of the invention, impedance probe 102 is used to identify the borders of a skin anomaly. Optionally, the probe is passed along a skin surface and according to the conductance the probe shows, it is determined whether the underlying tissue belongs to the anomaly. Alternatively or additionally, the determination of whether a specific region is part of the anomaly is responsive to any other dielectric parameter, such as a determined capacitance, phase and/or a combined function of such measures. In some embodiments of the invention, probe 102 includes a pencil and/or other marker which mark the anomaly. The pencil automatically imprints a mark on the tissue, when the impedance measurements of probe 102 determine that the pencil is above a border of the anomaly. Alternatively or additionally, the physician operates the pencil according to the impedance measurements.

Alternatively or additionally to using electrode head 112, other types of electrode heads may be used. For example, an electrode head with a plurality of arrays of sensing elements may be used. In some embodiments of the invention, an electrode head comprises a box shape with six surfaces. One of the surfaces comprises a plug or socket, and two or more of the surfaces comprise electrode arrays, for example similar to those described above with respect to electrode head 112.

Although the above embodiments employ an electrode head with small distances between sensing elements, e.g., tips 108, so as to achieve a fine resolution, in some embodiments of the invention, a probe with a larger distance between sensing elements and/or larger sensing elements may be used. The use of larger sensing elements, e.g., having an area of 4–25 mm$^2$, allows scanning a larger area in a single scan, although with a lower resolution. Optionally, the large sensing elements have a triangular pointed shape similar to the shape described above of tips 108. Alternatively, the larger sensing elements have a plurality of sharp points. In some embodiments of the invention, a sensing element comprises a circular or square crown shape in which the sharp points are on the outer circumference of the sensing element. In some embodiments, the outer circumference comprises a periodic structure in which each period includes one or more tips. In an exemplary embodiment of the invention, each period is between about 10–500 micrometers. Alternatively, the placement of the tips is not periodic. Rather, the outer circumference may have different shapes at different areas of the circumference. Alternatively, the sensing element comprises tips on substantially its entire peripheral surface.

The sharpness of the peaks, their separation from each other and/or their height are selected, in some embodiments, such that the peaks penetrate a patient's tissue surface to a predetermined depth. In some embodiments of the invention, the area of the portions of the sensing element which enter into the skin comprise at least a predetermined area of the sensing element so as to have a relatively large area which enters the skin and receives currents from the imaged area.

Alternatively, in some embodiments of the invention, to using corrugated or pointed sensing elements, flat, sensing elements may be used, for example for patients with high sensitivity.

The above described methods and apparatus may be used for identification of various types of skin cancer, including, but not limited to, Melanoma, Basal cell carcinoma (BCC) and Squamous cell carcinoma (SCC). In addition, the methods and apparatus may be used for identification of other dermatology conditions, such as psoriasis. The frequencies and/or other parameters used are optionally adjusted according to the specific skin condition to be identified.

Although the above scanning unit and electrode head were described as being used for skin scanning, one or more embodiments of the present invention may be used in scanning other body portions in which lesions are seen on the surface, for example, the cervix and/or rectum. Optionally, apparatus used for scanning the cervix and/or rectum includes flat electrodes which contact the surface, rather than tips 108, which slightly penetrate the surface. In addition, some of the embodiments of the invention, such as the structure of electrode head 112 and its size, may be used with other anomaly detection and analysis procedures, such as breast cancer detection.

Particularly, electrode head 112 is especially advantageous for procedures which include application and/or detection of electrical currents, in which the resistive top layer of the skin surface may substantially reduce the detected and/or applied currents.

It will be appreciated that the above described methods may be varied in many ways, including, changing the order of steps, and/or performing a plurality of steps concurrently. For example, the etching (404) of the conductive layer, described above with reference to FIG. 5, may be performed before the cutting (406) of the protruding portions of the wires into pointed shapes. It should also be appreciated that the above described description of methods and apparatus are to be interpreted as including apparatus for carrying out the methods, and methods of using the apparatus. The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

What is claimed is:

1. An electrode head including at least one bio-compatible electrode, comprising;
    a plurality of printed circuit boards (PCB), each having a face area and a thickness, attached along their face areas; and
    at least one bio-compatible electrode extending from the thickness of at least one of the plurality of printed circuit boards.

2. An electrode head according to claim 1, wherein the plurality of printed circuit boards are attached with an adhesive which has at least 70% alcohol resistance.

3. An electrode head according to claim 1, wherein the at least one electrode comprises at least one electrode extending from each of the plurality of printed circuit boards (PCBs).

4. An electrode head according to claim 3, wherein the at least one electrode extending from each of the plurality of PCBs comprises at least eight electrodes extending from each of the PCBs.

5. An electrode head according to claim 1, wherein the at least one electrode comprises a plurality of electrodes which are held by the electrode head at fixed relative positions.

6. An electrode head according to claim 1, comprising at least one leading wire running along the at least one of the plurality of PCBs and wherein the leading wire is formed as a single piece with one of the electrodes.

7. An electrode head according to claim 1, wherein the at least one electrode comprises at least one electrode tapered toward an end of the electrode, distal from the PCB.

8. An electrode head according to claim 1, wherein each of the PCBs is connected to at least one other PCB such that substantially all of its face area overlaps substantially all of the face area of the other PCB.

9. An electrode head including at least one bio-compatible electrode, comprising:
    a plurality of printed circuit boards (PCBs), each having a face area and a thickness; and
    a plurality of electrodes extending from the thickness of the printed circuit boards, the electrodes being held by the circuit boards at fixed relative positions.

10. An electrode head according to claim 9, wherein the plurality of electrodes comprise gold plated electrodes.

11. An electrode head including at least one bio-compatible electrode, comprising:
    a plurality of printed circuit boards (PCB), each having a face area and a thickness, each of the PCBs being positioned with respect to at least one other PCB such that at least a portion of its face area overlaps most of the face area of the other PCB; and
    at least one bio-compatible electrode extending from the thickness of at least one of the printed circuit boards.

12. An electrode head according to claim 11, wherein each of the PCBs is connected to at least one other PCB such that substantially all of its face area overlaps substantially all of the face area of the other PCB.

13. An electrode head according to claim 11, wherein the at least one electrode comprises at least one electrode extending from each of the plurality of printed circuit boards (PCBs).

14. An electrode head according to claim 13, wherein the at least one electrode extending from each of the plurality of PCBs comprises at least eight electrodes extending form each of the PCBs.

15. An electrode head according to claim 11, wherein the at least one electrode comprises a plurality of electrodes which are held by the electrode head at fixed relative positions.

16. An electrode head according to claim 11, wherein the at least one electrode comprises at least one electrode tapered toward an end of the electrode, distal from the PCB.

17. An electrode head including at least one bio-compatible electrode, comprising:
    a plurality of printed circuit boards (PCB), each having a face area and a thickness, each of the PCBs being positioned with respect to at least one other PCB such that at least a portion of its face area overlaps most of the face area of the other PCB; and
    at least one bio-compatible electrode extending from at least one of the printed circuit boards,
    wherein the plurality of printed circuit boards are attached with an adhesive which has at least 70% alcohol resistance.

18. An electrode head including at least one bio-compatible electrode, comprising;
    a plurality of printed circuit boards (PCB), each having a face area and a thickness, each of the PCBs being positioned with respect to at least one other PCB such that at least a portion of its face area overlaps most of the face area of the other PCB;
    at least one bio-compatible electrode extending from at least one of the printed circuit boards; and
    at least one leading wire running along at least one of the PCBs and wherein the leading wire is formed as a single piece with one of the electrodes.

* * * * *

UNITED STATES PATENT AND TRADEMARK OFFICE
CERTIFICATE OF CORRECTION

PATENT NO. : 6,788,966 B2
DATED : September 7, 2004
INVENTOR(S) : Gad Kenan

It is certified that error appears in the above-identified patent and that said Letters Patent is hereby corrected as shown below:

<u>Title page,</u>
Item [75], Inventors, cancel 2 inventors beginning with "Yael Agi" to and including "Zurit (IL)"

Signed and Sealed this

Fifteenth Day of March, 2005

JON W. DUDAS
*Director of the United States Patent and Trademark Office*